(12) United States Patent
Conway et al.

(10) Patent No.: US 11,661,611 B2
(45) Date of Patent: May 30, 2023

(54) GENETIC MODIFICATION OF CYTOKINE INDUCIBLE SH2-CONTAINING PROTEIN (CISH) GENE

(71) Applicant: Sangamo Therapeutics, Inc., Richmond, CA (US)

(72) Inventors: Anthony Conway, Richmond, CA (US); Gary K. Lee, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 1002 days.

(21) Appl. No.: 16/185,699

(22) Filed: Nov. 9, 2018

(65) Prior Publication Data

US 2019/0136261 A1 May 9, 2019

Related U.S. Application Data

(60) Provisional application No. 62/716,002, filed on Aug. 8, 2018, provisional application No. 62/583,724, filed on Nov. 9, 2017.

(51) Int. Cl.
  *C12N 15/85* (2006.01)
  *C12N 9/22* (2006.01)
  *A61K 48/00* (2006.01)

(52) U.S. Cl.
  CPC ........... *C12N 15/85* (2013.01); *C12N 9/22* (2013.01); *A61K 48/00* (2013.01); *C07K 2319/81* (2013.01)

(58) Field of Classification Search
  None
  See application file for complete search history.

(56) References Cited

U.S. PATENT DOCUMENTS

| | | |
|---|---|---|
| 5,176,996 A | 1/1993 | Hogan et al. |
| 5,420,032 A | 5/1995 | Marshall et al. |
| 5,422,251 A | 6/1995 | Fresco |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,833,252 B1 | 12/2004 | Dujon et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |
| 8,034,598 B2 | 10/2011 | Miller |
| 8,110,379 B2 | 2/2012 | DeKelver et al. |
| 8,153,773 B2 | 4/2012 | Jemielity et al. |
| 8,329,986 B2 | 12/2012 | Butler et al. |
| 8,399,218 B2 | 3/2013 | Gupta et al. |
| 8,409,861 B2 | 4/2013 | Guschin et al. |
| 8,563,314 B2 | 10/2013 | Gregory et al. |
| 8,585,526 B2 | 11/2013 | Beutler et al. |
| 8,623,618 B2 | 1/2014 | Doyon et al. |
| 8,697,359 B1 | 4/2014 | Zhang |
| 8,703,489 B2 | 4/2014 | Wang |
| 8,772,453 B2 | 7/2014 | Paschon et al. |
| 8,871,905 B2 | 10/2014 | Holmes et al. |
| 8,936,936 B2 | 1/2015 | Holmes et al. |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Charles A. Gersbach, Synthetic Zinc Finger Proteins: The Advent of Targeted Gene Regulation and Genome Modification Technologies. Acc. Chem. Res. 2014, 47, 2309-2318). (Year: 2014).*
Aaronson, et al., "A Road Map for Those Who Don't Know JAK-STAT," *Science* 296(5573):1653-1655 (2002).
Aman, et al., "CIS Associates With the Interleukin-2 Receptor Beta Chain and Inhibits Interleukin-2-Dependent Signaling," *J Biol Chem* 274(42):30266-30272 (1999).
Anderson, et al., "Maximal Expression of Suppressors of Cytokine Signaling in the Rat Ovary Occurs in Late Pregnancy," *Reproduction* 138(3):537-544 (2009).

(Continued)

*Primary Examiner* — Kagnew H Gebreyesus

(74) *Attorney, Agent, or Firm* — Foley & Lardner LLP

(57) ABSTRACT

The present disclosure is in the field of genome engineering, particularly targeted genetic modification of a CISH gene.

9 Claims, 6 Drawing Sheets

Specification includes a Sequence Listing.

(56) References Cited

U.S. PATENT DOCUMENTS

| | | | |
|---|---|---|---|
| 8,945,868 | B2 | 2/2015 | Collingwood et al. |
| 8,956,828 | B2 | 2/2015 | Bonini et al. |
| 9,005,973 | B2 | 4/2015 | Cost et al. |
| 9,045,763 | B2 | 6/2015 | DeKelver et al. |
| 9,150,847 | B2 | 10/2015 | Rebar |
| 9,200,266 | B2 | 12/2015 | Wang |
| 9,206,404 | B2 | 12/2015 | Cui et al. |
| 9,394,531 | B2 | 7/2016 | Miller |
| 9,394,545 | B2 | 7/2016 | Rebar |
| 9,458,205 | B2 | 10/2016 | Gregory et al. |
| 9,855,298 | B2 | 1/2018 | Bot et al. |
| 9,877,988 | B2 | 1/2018 | Rebar |
| 9,957,526 | B2 | 5/2018 | Holmes et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2005/0267061 | A1 | 12/2005 | Martin |
| 2006/0063231 | A1 | 3/2006 | Li et al. |
| 2007/0117128 | A1 | 5/2007 | Smith et al. |
| 2007/0218528 | A1 | 9/2007 | Miller |
| 2008/0159996 | A1 | 7/2008 | Ando et al. |
| 2009/0068164 | A1 | 3/2009 | Segal et al. |
| 2010/0218264 | A1 | 8/2010 | Cui et al. |
| 2011/0201055 | A1 | 8/2011 | Doyon et al. |
| 2011/0265198 | A1 | 10/2011 | Gregory et al. |
| 2012/0017290 | A1 | 1/2012 | Cui et al. |
| 2012/0195936 | A1 | 8/2012 | Rudolph et al. |
| 2013/0122591 | A1 | 5/2013 | Cost et al. |
| 2013/0137104 | A1 | 5/2013 | Cost et al. |
| 2013/0177960 | A1 | 7/2013 | Rebar |
| 2013/0177983 | A1 | 7/2013 | Rebar |
| 2014/0335063 | A1 | 11/2014 | Cannon et al. |
| 2015/0056705 | A1 | 2/2015 | Conway et al. |
| 2015/0064789 | A1 | 3/2015 | Paschon et al. |
| 2015/0139943 | A1 | 5/2015 | Campana et al. |
| 2017/0281682 | A1 | 10/2017 | Wilson et al. |
| 2018/0087072 | A1 | 3/2018 | Miller et al. |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2010/079430 A1 | 7/2010 |
| WO | 2017023803 A1 | 2/2017 |
| WO | WO-2017/100861 | 6/2017 |
| WO | WO-2018/075664 | 4/2018 |
| WO | WO-2018/081476 | 5/2018 |
| WO | WO-2019/032675 | 2/2019 |
| WO | WO-2019/213610 | 11/2019 |

OTHER PUBLICATIONS

Argast, et al., "I-PPOI and I-CREI Homing Site Sequence Degeneracy Determined by Random Mutagenesis and Sequential In Vitro Enrichment," *J. Mol. Biol.* 280(3):345-353 (1998).
Arun, et al., "Targeted Analysis Reveals an Important Role of JAK-STAT-SOCS Genes for Milk Production Traits in Australian Dairy Cattle," *Front Genet* 6:342 (2015).
Ashworth, et al., "Computational Redesign of Endonuclease DNA Binding and Cleavage Specificity," *Nature* 441:656-659 (2006).
Beerli, et al., "Engineering Polydactyl Zinc-Finger Transcription Factors," *Nature Biotechnology* 20:135-141 (2002).
Belfort, et al., "Homing Endonucleases: Keeping the House in Order," *Nucleic Acids Research* 25(17):3379-3388 (1997).
Bhattacharya, et al., "Granulocyte Macrophage Colony-Stimulating Factor and Interleukin-5 Activate STAT5 and Induce CIS1 MRNA in Human Peripheral Blood Eosinophils," *Am J Respir Cell Mol Biol* 24(3):312-316 (2001).
Blat, et al., "Suppression of Murine Colitis and Its Associated Cancer by Carcinoembryonic Antigen-Specific Regulatory T Cells," *Mol Ther* 22(5):1018-1028 (2014).
Boch, et al., "Breaking the Code of DNA Binding Specificity of TAL-Type III Effectors," *Science* 326:1509-1512 (2009).
Bonas, et al., "Genetic and Structural Characterization of the Avirulence Gene avrBs3 From *Xanthomonas campestris* PV. *vesicatoria*," *Molecular and General Genetics* 218:127-136 (1989).
Chen, et al., "Functional Association of Cytokine-Induced SH2 Protein and Protein Kinase C in Activated T Cells," *Int Immunol* 15(3):403-409 (2003).
Chevalier, et al., "Design, Activity, and Structure of a Highly Specific Artificial Endonuclease," *Molec. Cell* 10(4):895-905 (2002).
Choo, et al., "Advances in Zinc Finger Engineering," *Current Opinion in Structural Biology* 10:411-416 (2000).
Christian, et al., "Targeting DNA Double-Strand Breaks With TAL Effector Nucleases," *Genetics* 186(2):757-761 epub 10.1534/genetics.110.120717 (2010).
Clasen, et al., "Gene Expression in Skeletal Muscle After an Acute Intravenous GH Bolus in Human Subjects: Identification of a Mechanism Regulating ANGPTL4," *J Lipid Res* 54(7):1988-1997 (2013).
Cong, et al., "Multiplex Genome Engineering Using CRISPR/CAS Systems," *Science Express* 7 pgs. 1/10.1126/science 1231143 (2013).
Dujon, et al., "Mobile Introns: Definition of Terms and Recommended Nomenclature," *Gene* 82(1):115-118 (1989).
Endo, et al., "CIS1 Interacts With the Y532 of the Prolactin Receptor and Suppresses Prolactin-Dependent STAT5 Activation," *J Biochem* 133(1):109-113 (2003).
Epinat, et al., "A Novel Engineered Meganuclease Induces Homologous Recombination in Yeast and Mammalian Cells," *Nucleic Acids Res.* 31(11):2952-2962 (2003).
Esteves, et al., "Human Leptospirosis: Seroreactivity and Genetic Susceptibility in the Population of São Miguel Island (Azores, Portugal)," *PLoS One* 9(9):e108534 (2014).
Fagerlund, et al., "The CPF1 CRISPR-CAS Protein Expands Genome-Editing Tools," (2015) *Genom Bio* 16(251) 3 pgs. (2015).
Gimble, et al., "Substrate Recognition and Induced DNA Distortion by the PI-SCEI Endonuclease, an Enzyme Generated by Protein Splicing," *J. Mol. Biol.* 263:163-180 (1996).
Guo, et al., "Directed Evolution of an Enhanced and Highly Efficient FOKI Cleavage Domain for Zinc Finger Nucleases," *Journal of Molecular Biology* 400(1):96-107 (2010).
Haft, et al., "A Guild of 45 CRISPR-Associated (Cas) Protein Families and Multiple CRISPR/Cas Subtypes Exist in Prokaryotic Genomes," *PLoS Computational Biology* 1(6):e60 (2005).
Heuer, et al., "Repeat Domain Diversity of avrBs3-Like Genes in *Ralstonia solanacearum* Strains and Association With Host Preferences in the Field," *Applied and Environmental Microbiology* 73(13):4379-4384 (2007).
Hu, et al., "Polymorphisms in CISH Gene Are Associated With Persistent Hepatitis B Virus Infection in Han Chinese Population," *PLoS One* 9(6):e100826 (2014).
Isalan et al., "A Rapid, Generally Applicable Method to Engineer Zinc Fingers Illustrated by Targeting the HIV-1 Promoter," *Nature Biotechnology* 19(7):656-660 (2001).
Jansen, et al., "Identification of Genes That Are Associated With DNA Repeats in Prokaryotes," *Molecular Microbiology* 43(6):1565-1575 (2002).
Jasin, "Genetic Manipulation of Genomes With Rare-Cutting Endonucleases," *Trends Genet.* 12(6):224-228 (1996).
Jatiani, et al., "JAK/STAT Pathways in Cytokine Signaling and Myeloproliferative Disorders: Approaches for Targeted Therapies," *Genes Cancer* 1(10):979-93 (2010).
Ji, et al., "Polymorphisms in the CISH Gene Are Associated With Susceptibility to Tuberculosis in the Chinese Han Population," *Infect Genet Evol* 28:240-4 (2014).

(56) References Cited

OTHER PUBLICATIONS

Jinek, et al., "A Programmable Dual-RNA-Guided DNA Endonuclease in Adaptive Bacterial Immunity," Science 337:816-821 (2012).
Jinek, et al., "RNA-Programmed Genome Editing in Human Cells," eLife 2:e00471. DOI: 10.7554/eLife.00471 (2013).
Kay, et al., "A Bacterial Effector Acts as a Plant Transcription Factor and Induces a Cell Size Regulator," Science 318:648-651 (2007).
Kershaw, et al., "Regulation of Janus Kinases by SOCS Proteins," Biochem Soc Trans. 41(4):1042-7 (2013).
Khor, et al., "CISH and Susceptibility to Infectious Diseases," N Engl J Med 362(22):2092-101 (2010).
Kormann, et al, Expression of Therapeutic Proteins After Delivery of Chemically Modified mRNA in Mice, Nature Biotechnology 29(2):154-157 (2011).
Landsman, et al., "Role of the Cytokine-Induced SH2 Domain-Containing Protein CIS in Growth Hormone Receptor Internalization," J Biol Chem 280(45):37471-80 (2005).
Li, et al., "Cytokine-Induced SRC Homology 2 Protein (CIS) Promotes T Cell Receptor-Mediated Proliferation and Prolongs Survival of Activated T Cells," J Exp Med 191(6):985-94 (2000).
Makarova, et al., "A DNA Repair System Specific for Thermophilic Archaea and Bacteria Predicted by Genomic Context Analysis," Nucleic Acids Research 30(2):482-496 (2002).
Makarova, et al., "A Putative RNA-Interference-Based Immune System in Prokaryotes: Computational Analysis of the Predicted Enzymatic Machinery, Functional Analogies With Eukaryotic RNAi, And Hypothetical Mechanisms of Action," Biology Direct 1:7 (2006).
Matsumoto, et al., "CIS, A Cytokine Inducible SH2 Protein, Is a Target of the JAK-STAT5 Pathway and Modulates STAT5 Activation," Blood 89(9):3148-54 (1997).
Matsumoto, et al., "Suppression of STAT5 Functions in Liver, Mammary Glands, And T Cells in Cytokine-Inducible SH2-Containing Protein 1 Transgenic Mice," Mol Cell Biol 19(9):6396-407 (1999).
Moscou, et al., "A Simple Cipher Governs DNA Recognition by TAL Effectors," Science 326:1501 (2009).
Olovnikov, et al., "Bacterial Argonaute Samples the Transcriptome to Identify Foreign DNA," Molecular Cell 51:594-605 (2013).
Pabo, et al., "Design and Selection of Novel $CYS_2$—$HIS_2$ Zinc Finger Proteins," Ann. Rev. Biochem. 70:313-340 (2001).
Palmer, et al., "Suppressors of Cytokine Signaling (SOCS) in T Cell Differentiation, Maturation, and Function," Trends Immunol 30(12):592-602 (2009).
Palmer, et al., "CISH Actively Silences TCR Signaling in CD8+ T Cells to Maintain Tumor Tolerance," J Exp Med 212(12):2095-113 (2015).
Paques, et al., "Meganucleases and DNA Double-Strand Break-Induced Recombination: Perspectives for Gene Therapy," Current Gene Therapy 7:49-66 (2007).
Pardoll, "The Blockade of Immune Checkpoints in Cancer Immunotherapy," Nat Rev Cancer 12(4):252 (2012).
Perez, et al., "Establishment of HIV-1 Resistance in CD4+ T Cells by Genome Editing Using Zinc-Finger Nucleases," Nature Biotechnology 26(7):808-816 (2008).
Perler, et al., "Protein Splicing Elements : Inteins and Exteins—A Definition of Terms and Recommended Nomenclature," Nucleic Acids Res. 22(7): 1125-1127 (1994).
Raccurt, et al., "Suppressor of Cytokine Signalling Gene Expression is Elevated in Breast Carcinoma," Br. J. Cancer 89(3):524-32 (2003).
Ram, et al., "SOCS/CIS Protein Inhibition of Growth Hormone-Stimulated STAT5 Signaling by Multiple Mechanisms," J Biol Chem 274(50):35553-61 (1999).
Ran, et al., "In Vivo Genome Editing Using Staphylococcus aureus CAS9," Nature 520:186 (2015).
Rawlings, et al., "The JAK/STAT Signaling Pathway," J Cell Sci 117(Pt 8):1281-3 (2004).
Sadowski, et al., "A Noncatalytic Domain Conserved Among Cytoplasmic Protein-Tyrosine Kinases Modifies the Kinase Function and Transforming Activity of Fujinami Sarcoma Virus P130GAG-FPS," Mol Cell Biol 6(12):4396-408 (1986).
Sallusto, et al., "Two Subsets of Memory T Lymphocytes With Distinct Homing Potentials and Effector Functions," Nature 401(6754):708-12 (1999).
Schornack, et al., "Gene-For-Gene-Mediated Recognition of Nuclear-Targeted AVRBS3-Like Bacterial Effector Proteins," Journal of Plant Physiology 163(3):256-272 (2006).
Segal, et al., "Custom DNA-Binding Proteins Come of Age: Polydactyl Zinc-Finger Proteins," Current Opinion in Biotechnology 12:632-637 (2001).
Sheng, et al., "Structure-Based Cleavage Mechanism of Thermus Thermophilus Argonaute DNA Guide Strand-Mediated DNA Target Cleavage," Proc. Natl. Acad. Sci. U.S.A. 111(2):652-657 (2014).
Sun, et al., "Genetic Contribution of CISH Promoter Polymorphisms to Susceptibility to Tuberculosis in Chinese Children," PLoS 9(3):e92020 (2014).
Swarts, et al., "DNA-Guided DNA Interference by a Prokaryotic Argonaute" Nature 507(7491):258-261 (2014).
Tebas, et al., "Gene Editing of CCR5 in Autologous CD4 T Cells of Persons Infected With HIV," New Eng J Med 370(10):901-910 (2014).
Tong, et al., "Association of CISH-292A/T Genetic Variant With Hepatitis B Virus Infection," Immunogenetics 64(4):261-5 (2012).
Trengove, et al., "SOCS Proteins in Development and Disease," Am J Clin Exp Immunol 2(1):1-29 (2013).
Urnov, et al., "Highly Efficient Endogenous Human Gene Correction Using Designed Zinc-Finger Nucleases," Nature 435(7042):646-651 (2005).
Vogel, "A Bacterial Seek-And-Destroy System for Foreign DNA," Science 344(6187):972-973 (2014).
Wang, et al., "New Development in CAR-T Cell Therapy," J. Hematol Oncol 10(1):53 (2017).
Welte, et al., "STAT5 Interaction With the T Cell Receptor Complex and Stimulation of T Cell Proliferation," Science 283(5399):222-5 (1999).
Yang, et al., "The Signaling Suppressor CIS Controls Proallergic T Cell Development and Allergic Airway Inflammation," Nat Immunol 14(7):732-40 (2013).
Yoshimura, et al, "A Novel Cytokine-Inducible Gene CIS Encodes an SH2-Containing Protein That Binds to Tyrosine-Phosphorylated Interleukin 3 and Erythropoietin Receptors," EMBO J 14(12):2816-26 (1995).
Yoshimura, et al., "SOCS Proteins, Cytokine Signalling and Immune Regulation," Nat Rev Immunol 7(6):454-65 (2007).
Yu, et al., "An Engineered VEGF-Activating Zinc Finger Protein Transcription Factor Improves Blood Flow and Limb Salvage in Advanced-Age Mice," FASEB J. 20(3):479-481 (2006).
Yuan, et al., "Crystal Structure of A. aeolicus Argonaute, A Site-Specific DNA-Guided Endoribonuclease, Provides Insights Into RISC-Mediated mRNA Cleavage," Molecular Cell 19:405-419 (2005).

* cited by examiner

GENETIC MODIFICATION OF CYTOKINE INDUCIBLE SH2-CONTAINING PROTEIN (CISH) GENE

CROSS-REFERENCE TO RELATED APPLICATIONS

The present application claims the benefit of U.S. Provisional Application No. 62/583,724, filed Nov. 9, 2017 and U.S. Provisional Application No. 62/716,002, filed Aug. 8, 2018, the disclosures of which are hereby incorporated by reference in their entireties.

SEQUENCE LISTING

The instant application contains a Sequence Listing which has been submitted electronically in ASCII format and is herein incorporated in its entirety. Said ASCII copy, created on Jun. 23, 2022, is named "128687_1965_SL.txt" and is 13,868 bytes in size.

TECHNICAL FIELD

The present disclosure is in the field of genome engineering, particularly targeted modification of a cytokine inducible SH2-containing protein (CISH or CIS) gene.

BACKGROUND

Cells communicate with each other either by direct contact or by releasing molecular "messages" into the extracellular space to coordinate proliferation, migration, differentiation and affect changes in gene expression in target cells expressing the appropriate cell surface receptor complexes. For many cytokines and growth factors, receptor binding initiates signal transduction within the target cells by the JAK/STAT signaling pathway. See, e.g., Aaronson, et al. (2002) *Science* 296(5573):1653-5; Rawlings, et al. (2004) *J Cell Sci* 117(Pt 8):1281-3; and Jatiani, et al. (2010) *Genes Cancer* 1(10):979-93. In the absence of ligand, the cytoplasmic end of the receptor is associated with inactive members of the Janus tyrosine kinase family (JAK1-3 or Tyk2). Ligand binding induces the formation of a receptor complex between two or more receptor subunits bringing the JAK proteins into close proximity allowing activation via trans-phosphorylation. The activated JAKs can then phosphorylate tyrosine residues on the cytoplasmic domain of the receptor to create a binding site for one of the signal transducers and activators of transcription (STAT) proteins.

There are seven STAT proteins in mammals, STAT1-4, STAT5a, STAT5b and STATE. Within the structure of each STAT protein is a Src homology-2 (SH2) domain (see, Sadowski, et al. (1986) *Mol Cell Biol* 6(12):4396-408) that directs binding to the phosphotyrosine containing site on the receptor where the STAT protein can itself be tyrosine phosphorylated by the JAK kinase. Once phosphorylated, the STAT proteins form homo- or heterodimers and are transported to the nucleus where they bind to DNA and stimulate transcription of nearby genes. Since the JAK/STAT pathway plays a key role in the regulation of growth, cell proliferation and immune response, dysregulation of this system can contribute to the development of cancer or inflammatory disease.

STAT activation rapidly induces expression of set of genes encoding the suppressor of cytokine signaling (SOCS) and cytokine-induced SH2 (CISH) domain-containing family of intracellular proteins. See, e.g., Palmer, et al. (2009) 30(12):592-602; Yoshimura, et al. (2007) *Nat Rev Immunol* 7(6):454-65; Trengove, et al. (2013) *Am J Clin Exp Immunol* 2(1):1-29. The SOCS/CISH proteins contain an N-terminal domain of variable sequence and function followed by an SH2 domain and a C terminal SOCS domain that directs assembly of an E3 ubiquitin ligase complex that labels target proteins with ubiquitin, marking them for degradation via the proteasome. The SOCS/CISH proteins inhibit JAK/STAT signaling by competing with STAT for binding to the phosphotyrosine site on the receptor, thereby inhibiting STAT activation, and by directing ubiquitin deposition on various proteins enhancing their turnover. Thus, the SOCS/CISH proteins establish a classic negative-feedback loop to modulate cytokine and growth factor signaling, and to enhance decay of the signal when the ligand is no longer present. Some SOCS proteins have additional activities, such as direct inhibition of the JAKs and enhancing turnover of other SOCS proteins, contributing further complexity to the regulation of receptor signal transduction. See, Kershaw, et al. (2013) *Biochem Soc Trans.* 41(4):1042-7.

CISH (also known as CIS) was the first SOCS protein identified as a gene rapidly induced (within 30 min) after ligand binding on the erythropoietin (EPO) receptor (EPOR). See, Yoshimura, et al. (1995) *EMBO J* 14(12): 2816-26. CISH expression was also induced by interleukin-2 (IL-2), IL-3 and granulocyte-macrophage colony-stimulating factor (GM-CSF) in the appropriate cell types. Immunoprecipitation analysis demonstrated that the CISH protein bound stably to the IL-3R beta chain and the EPOR, but only after ligand binding, suggesting that tyrosine phosphorylation of receptor was required. Over-expression of the CISH protein suppressed cell growth, indicating that CISH had a negative effect on signal transduction. Subsequently, CISH expression was shown to be dependent on STAT5 activation, and several STAT5 binding sites were found in the CISH promoter region. See, Matsumoto, et al. (1997) *Blood* 89(9):3148-54. Moreover, CISH inhibited EPO-dependent activation of STAT5 and suppressed activity of other STAT5-dependent receptors, indicating that CISH is a feedback modulator for STAT5.

A wide variety of STAT5-dependent receptors induce CISH expression, including (but not limited to) growth hormone (GH), prolactin (PRL), thrombopoietin (TPO), leptin, IL-2, IL-5 and IL-9. See, Bhattacharya, et al. (2001) *Am J Respir Cell Mol Biol* 24(3):312-6. CISH has been shown to bind and inhibit signaling from the GH receptor (GHR), the PRL receptor, and IL-2 receptor beta-chain, and to promote internalization and deactivation of the GHR. See, Ram, et al. (1999) *Biol Chem* 274(50):35553-61; Endo, et al. (2003) *J Biochem* 133(1): 109-13; Aman, et al. (1999) *J Biol Chem* 274(42):30266-72; Landsman, et al. (2005) *J Biol Chem* 280(45):37471-80. Expression of Cish mRNA is found in a number of tissues (liver, kidney, heart stomach, lung, ovary and skeletal muscle). See, Palmer, et al. (2009) 30(12):592-602; Anderson, et al. (2009) 138(3):537-44; Clasen, et al. (2013) *J Lipid Res* 54(7):1988-97. In spite of its apparent involvement in the signaling apparatus of a large number of important cytokines and growth factors, Cish knockout mice have minimal defects (except for subtle changes in the immune response). See, Palmer, et al. (2009) *Trends Immunol* 30(12):592-602; Trengove, et al. (2013) *Am J Clin Exp Immunol* 2(1):1-29. This may be due to compensatory activity of the other SOCS family proteins. An effect of CISH on the biology of putative target genes was observed in transgenic mice constitutively expressing Cish driven from the beta-actin promoter. Those mice had reduced body weight, defects in mammary gland development and reduced numbers of gamma/delta T cells, natural killer (NK) cells and NKT cells, a phenotype that resembled Stat5a and/or Stat5b deficient mice. See, Matsumoto, et al. (1999) *Mol Cell Biol* 19(9):6396-407.

Since CISH potentially influences signaling by many cytokines and growth factors, it is not surprising that CISH activity and variants have been found to be associated with infectious disease and cancer. Several studies have shown increased susceptibility to various infectious agents in subjects carrying certain CISH polymorphisms, including malaria, leptospirosis, hepatitis B virus and tuberculosis. See, Khor, et al. (2010) *N Engl J Med* 362(22):2092-101; Esteves, et al. (2014) *PLoS One* 9(9):e108534; Hu, et al. (2014) *PLoS One* 9(6):e100826; Tong, et al. (2012) *Immunogenetics* 64(4):261-5; Ji, et al. (2014) *Infect Genet Evol* 28:240-4; Sun, et al. (2014) *PLoS* 9(3):e92020. One risk allele common to all studies (r5414171, −292 from the start of transcription) displayed lower levels of CISH expression in peripheral blood mononuclear cells compared to the alternate allele. See, Khor and Sun, supra. In breast cancer, expression levels of CISH were elevated in breast carcinomas and cancer cell lines compared to normal tissues, leading to speculation that CISH may contribute to tumorigenesis by its ability to activate the extracellular-signal-regulated kinase (ERK). Raccurt, et al. (2003) *Br. J Cancer* 89(3):524-32. CISH variants are also associated with milk production traits in dairy cattle. See, Arun, et al. (2015) *Front Genet* 6:342.

Though the T cells do not utilize the classic JAK/STAT signaling pathway when responding to stimulation via the T cell receptor (TCR), Cish expression is rapidly induced (within 30 min) when T cells are activated by antibody to CD3. See, Ji, supra; Chen, et al. (2003) *Int Immunol* 15(3): 403-9; Palmer, et al. (2015) *J Exp Med* 212(12):2095-113; Yang, et al. (2013) *Nat Immunol* 14(7):732-40. STAT5 is rapidly phosphorylated after TCR stimulation, probably by the TCR-associated lymphocyte-specific protein tyrosine kinase (Lck). See, Welte, et al. (1999) *Science* 283(5399): 222-5. IL-2 expression is also induced by TCR stimulation, but with kinetics too slow to explain Cish induction. See, Yang, et al., supra; Li, et al. (2000) *J Exp Med* 191(6):985-94. In vivo, Cish expression was low in antigen-naïve T cells, but progressively increased in antigen-experienced central memory (TCM) and effector memory (TEM) CD8+ T cells collected after vaccination. See, Sallusto, et al. (1999) *Nature* 401(6754):708-12.

The role of Cish in T cell responsiveness has also been examined. Transgenic expression of Cish in vivo from the CD4 promoter generated mice with constitutive expression in the CD4+ helper T cell compartment. See, Li, et al., supra. Circulating T cell sub-populations were not affected, but instead of the expected suppressed responsiveness, CD4+ T cells displayed heightened TCR-induced proliferation and cytokine expression and increased survival in vitro. Circulating T cell populations were also normal in Cish knock-out mice, but again an enhanced response (proliferation and cytokine production) to TCR stimulation was observed in vitro in both the CD4+ and CD8+ T cell subsets. See, Palmer and Yang, supra. The molecular basis for Cish action is also unclear as the enhanced responsiveness of CD4+ T cells in Cish transgenic mice was attributed to an interaction between Cish and protein kinase C theta, while the inhibition of CD8 T cell activity by Cish was attributed to enhanced degradation of phospholipase C-gamma 1.

One consequence of enhanced T cell activity in Cish deficient mice was a durable and more aggressive response of adoptively transferred antigen-specific CD8 T cells to established tumors in a melanoma model. See, Palmer, supra. In addition, reducing CISH expression in human T cells enhanced the functionality of co-transduced tumor-specific TCRs. These data suggest that alleviating some of the negative feedback activity that moderates TCR signaling could produce more potent immune reactivity to a tumor. However, increased anti-melanoma activity in a mouse model was associated with greater ocular autoimmunity. Similarly, even though there were no large developmental defects in the other line of Cish deficient mice, spontaneous pulmonary disease developed in older animals (>6 months), apparently caused by enhanced development of TH2 and TH9 CD4 T cell subsets. These studies illustrate the common challenges with immunomodulation; too much suppression leaves the patient vulnerable to infection and tumor development, and too much stimulation can lead to autoimmunity or chronic inflammatory disease.

Recombinant transcription factors comprising the DNA binding domains from zinc finger proteins ("ZFPs") or TAL-effector domains ("TALEs") and engineered nucleases including zinc finger nucleases ("ZFNs"), TALENs, CRISPR/Cas nuclease systems, and homing endonucleases that are all designed to specifically bind to target DNA sites have the ability to regulate gene expression of endogenous genes and are useful in genome engineering, gene therapy and treatment of disorders such as cancer and inflammation. See, e.g., U.S. Pat. Nos. 9,877,988; 9,394,545; 9,150,847; 9,206,404; 9,045,763; 9,005,973; 8,956,828; 8,936,936; 8,945,868; 8,871,905; 8,586,526; 8,563,314; 8,329,986; 8,399,218; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publication Nos. 2003/0232410; 2005/0208489; 2005/0026157; 2005/0064474; 2006/0063231; 2008/0159996; 2010/0218264; 2012/0017290; 2011/0265198; 2013/0137104; 2013/0122591; 2013/0177983; 2013/0177960; and 2015/0056705, the disclosures of which are incorporated by reference in their entireties for all purposes. Further, targeted nucleases are being developed based on the Argonaute system (e.g., from *T. thermophilus*, known as 'TtAgo', see Swarts, et al. (2014) *Nature* 507(7491): 258-261), which also may have the potential for uses in genome editing and gene therapy.

Nuclease-mediated gene therapy can be used to genetically engineer a cell to have one or more inactivated genes and/or to cause that cell to express a product not previously being produced in that cell (e.g., via transgene insertion and/or via correction of an endogenous sequence). Examples of uses of transgene insertion include the insertion of one or more genes encoding one or more novel therapeutic proteins, insertion of a coding sequence encoding a protein that is lacking in the cell or in the individual, insertion of a wild-type gene in a cell containing a mutated gene sequence, and/or insertion of a sequence that encodes a structural nucleic acid such as shRNA or siRNA. Examples of useful applications of 'correction' of an endogenous gene sequence include alterations of disease-associated gene mutations, alterations in sequences encoding splice sites, alterations in regulatory sequences and targeted alterations of sequences encoding structural characteristics of a protein. Transgene constructs can be inserted by either homology directed repair (HDR) or by end capture during non-homologous end joining (NHEJ) driven processes. See, e.g., U.S. Pat. Nos. 9,045,763; 9,005,973; 7,888,121; and 8,703,489.

Clinical trials using these engineered transcription factors and nucleases have shown that these molecules are capable of treating various conditions, including cancers, HIV and/or blood disorders (such as hemoglobinopathies and/or hemophilias). See, e.g., Yu, et al. (2006) *FASEB J.* 20:479-481; Tebas, et al. (2014) *New Eng. J Med* 370(10):901. Thus, these approaches can be used for the treatment of diseases.

However, there remains a need for additional methods and compositions for CISH gene correction and donor delivery for treatment and/or prevention of cancer, inflammatory disorders and other disease in which CISH regulation is desired.

SUMMARY

The present invention describes compositions and methods for use in gene therapy and genome engineering. Specifically, the methods and compositions described relate to nuclease-mediated genomic modification (e.g., one or more insertions and/or deletions) of an endogenous CISH gene (mutant or wild-type). The genomic modification(s) may comprise insertions and/or deletions ("indels") that inactivate the target gene (e.g., via NHEJ following cleavage of the gene by the nuclease); targeted insertion of a transgene (donor) including a protein-encoding sequence, for example a protein that is lacking or deficient in a subject with a cancer or inflammatory condition and/or targeted insertion of a corrective donor (e.g., a sequence that restores functional CISH in a cell with a mutant gene), a chimeric antigen receptor (CAR) and/or one or more components or regulators of, or fusion proteins comprising an HLA complex (e.g., B2M-HLA-E or B2M-HLA-G fusion protein). The genetic modifications and/or cells comprising these modifications may be used in ex vivo or in vivo methods.

In certain aspects, provided herein is a genetically modified cell comprising a genomic modification within exon 2 or exon 3 of an endogenous CISH gene. Populations of the these genetically modified cells are also provided. The genomic modification may comprise one or more insertions and/or deletions (indels) and/or integration of one or more transgenes into the CISH gene (e.g., a transgene encodes a chimeric antigen receptor (CAR), an immunomodulating factor (e.g., PD1, CTLA-4, etc.), an engineered or exogenous T cell receptor (TCR) (e.g., an an antibody-coupled T-cell receptors (ACTR)). In certain aspects, the CISH gene is modified following cleavage by a nuclease (e.g., one or more zinc finger nucleases, one or more TALENs and/or one or more CRISPR/Cas nuclease systems). In certain embodiments, the nuclease comprises a DNA-binding domain that binds to a target site as shown in Table 2, for example a zinc finger nuclease comprising a zinc finger protein comprising 4, 5, or 6 zinc finger domains comprising a recognition helix such as the zinc finger proteins comprising the recognition helix regions of the proteins designated SBS #59488, SBS #59489, SBS #59440, SBS #59441, SBS #59558, SBS #59557, SBS #59581 or SBS #59580. Also provided are genetically modified cells (and populations of such cells) descended from any of the cells described herein. In some embodiments, cell is selected from the group consisting of a hematopoietic stem cell, a T effector cell and a T regulatory cell.

In other aspects, provided herein is a zinc finger protein comprising 6 zinc finger domains each comprising a recognition helix region, wherein the zinc finger protein comprises the recognition helix regions of the proteins designated SBS #59488, SBS #59489, SBS #59440, SBS #59441, SBS #59558, SBS #59557, SBS #59581 or SBS #59580. Fusion proteins comprising any of the zinc finger proteins described herein are also provided, including fusions of the zinc finger protein with a wild-type or engineered cleavage domain or cleavage half-domain. One or more polynucleotides encoding one or more of the ZFPs and/or fusion proteins described herein are also provided. Isolated cells (e.g., T effector cells, a T regulatory cells and/or hematopoietic stem cells) comprising one or more of the proteins (e.g., ZFPs or fusion proteins) and/or one or more of the polynucleotides encoding these proteins are also provided. Kits comprising one or more of the proteins, one or more of the polynucleotides and/or one or more isolated cells described herein are also provided.

In other aspects, the invention provides a method of generating a genetically modified cell as described herein, the method comprising introducing, into the cell, one or more polynucleotides encoding one or more nucleases comprising a DNA-binding domain that binds to target site in exon 2 or exon 3 of the CISH gene, wherein the nuclease bind to and cleave the CISH gene, thereby genetically modifying the cell. In certain embodiments, the genetically modified cell comprises a transgene that is integrated into the CISH gene and expressed in the cell. Also provided is a method of providing a protein to a subject in need thereof, the method comprising administering a genetically modified cell as described herein, wherein the cell expresses the transgene (e.g., CAR, immunomodulating factor, and/or ACTR, etc.) in the subject.

In one aspect, disclosed herein are methods and compositions for targeted modification of a CISH gene using one or more nucleases. Nucleases, for example engineered meganucleases, zinc finger nucleases (ZFNs) (the term "a ZFN" includes a pair of ZFNs), TALE-nucleases (TALENs including fusions of TALE effectors domains with nuclease domains from restriction endonucleases and/or from meganucleases (such as mega TALEs and compact TALENs) (the term "a TALEN" includes a pair of TALENs), Ttago system and/or CRISPR/Cas nuclease systems are used to cleave DNA at a CISH gene locus in the cell. The CISH gene may be inactivated following cleavage (e.g., by insertions and/or deletions ("indels")) and/or by targeted insertion of a donor transgene. The donor transgene may be via homology directed repair (HDR) or non-homology repair mechanisms (e.g., NHEJ donor capture). The nucleases described herein can induce a double-stranded (DSB) or single-stranded break (nick) in the target DNA. In some embodiments, two nickases are used to create a DSB by introducing two nicks. In some cases, the nickase is a ZFN, while in others, the nickase is a TALEN or a CRISPR/Cas nickase. Any of the nucleases described herein (e.g., ZFNs, TALENs, CRISPR/Cas etc.) may target an intron and/or an exon (e.g., exon 2 or 3) of a CISH gene (including sequences overlapping introns and exons), for instance the target sequences shown Table 2, including for example a target site comprising 9 to 20 or more (9, 10, 11, 12, 13, 14, 15, 16, 17, 18, 19, 20 or more) contiguous or non-contiguous amino acids of the sequences shown in Table 2.

In one aspect, described herein is a non-naturally occurring zinc-finger protein (ZFP) that binds to a target site in a CISH gene in a genome, wherein the ZFP comprises one or more engineered zinc-finger binding domains. In one embodiment, the ZFP is a zinc-finger nuclease (ZFN) that cleaves a target genomic region of interest, wherein the ZFN comprises one or more engineered zinc-finger binding domains and a nuclease cleavage domain or cleavage half-domain. Cleavage domains and cleavage half domains can be obtained, for example, from various restriction endonucleases and/or homing endonucleases and may be wild-type or engineered (mutant). In one embodiment, the cleavage half-domains are derived from a Type IIS restriction endonuclease (e.g., FokI). In certain embodiments, the zinc finger domain a zinc finger protein with the recognition helix domains ordered as shown in a single row of Table 1. Nucleases comprising these zinc finger proteins may include any linker sequence (e.g., linking it to the cleavage domain) and any cleavage domain (e.g., a dimerization mutant such as an ELD mutant; a FokI domain having mutation at one or more of 416, 422, 447, 448, and/or 525; and/or catalytic domain mutants that result in nickase functionality). See, e.g., U.S. Pat. Nos. 8,703,489; 9,200,266; 8,623,618; and 7,914,796; and U.S. Patent Publication No. 2018/0087072. In certain embodiments, the ZFP of the ZFN binds to a target site of 9 to 18 or more nucleotides within the sequence shown in Table 2 (SEQ ID NO:40-47).

In another aspect, described herein is a Transcription Activator Like Effector (TALE) protein that binds to target site (e.g., a target site comprising at least 9 or 12 (e.g., 9 to 20 or more) nucleotides of a target sequence as shown in Table 2, SEQ ID NO:40-47) in a CISH gene in a genome, wherein the TALE comprises one or more engineered TALE binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains can be obtained, for example, from various restriction endonucleases and/or homing endonucleases (meganuclease). In one embodiment, the cleavage half-domains are derived from a Type IIS restriction endonuclease (e.g., FokI). In other embodiments, the cleavage domain is derived from a meganuclease, which meganuclease domain may also exhibit DNA-binding functionality.

In another aspect, described herein is a CRISPR/Cas system that binds to target site in a CISH gene in a genome, wherein the CRISPR/Cas system comprises one or more engineered single guide RNA or a functional equivalent, as well as a Cas9 nuclease. In certain embodiments, the single guide RNA (sgRNA) binds to a sequence comprising 9, 12 or more contiguous nucleotides of a target site as shown in Table 2 (SEQ ID NO:40-47).

The nucleases (e.g., ZFN, CRISPR/Cas system, Ttago and/or TALEN) as described herein may bind to and/or cleave the region of interest in a coding or non-coding region within or adjacent to the CISH gene, such as, for example, a leader sequence, trailer sequence or intron, or within a non-transcribed region, either upstream or downstream of the coding region.

In another aspect, described herein is a polynucleotide encoding one or more nucleases (e.g., ZFNs, CRISPR/Cas systems, Ttago and/or TALENs described herein). The polynucleotide may be, for example, mRNA. In some aspects, the mRNA may be chemically modified (See e.g. Kormann, et al. (2011) *Nature Biotechnology* 29(2): 154-157).

In another aspect, described herein is a ZFN, CRISPR/Cas system, Ttago and/or TALEN expression vector comprising a polynucleotide, encoding one or more nucleases (e.g., ZFNs, CRISPR/Cas systems, Ttago and/or TALENs) as described herein, operably linked to a promoter. In one embodiment, the expression vector is a viral vector (e.g., an AAV vector). In one aspect, the viral vector exhibits tissue specific tropism.

In another aspect, described herein is a host cell comprising one or more nuclease (e.g., ZFN, CRISPR/Cas systems, Ttago and/or TALEN) expression vectors.

In another aspect, pharmaceutical compositions comprising an expression vector as described herein are provided. In some embodiments, the pharmaceutical composition may comprise more than one expression vector. In some embodiments, the pharmaceutical composition comprises a first expression vector comprising a first polynucleotide, and a second expression vector comprising a second polynucleotide. In some embodiments, the first polynucleotide and the second polynucleotide are different. In some embodiments, the first polynucleotide and the second polynucleotide are substantially the same. The pharmaceutical composition may further comprise a donor sequence (e.g., a transgene encoding a protein lacking or deficient in a disease or disorder such as an LSD or a hemophilia). In some embodiments, the donor sequence is associated with an expression vector.

In some embodiments, a fusion protein comprising a CISH DNA-binding domain (e.g., zinc finger protein or TALE or sgRNA or meganuclease) and a wild-type or engineered cleavage domain or cleavage half-domain are provided.

The nucleases described herein may bind to and/or cleave a CISH gene within the coding region of the gene or in a non-coding sequence within or adjacent to the gene, such as, for example, a leader sequence, trailer sequence or intron, or within a non-transcribed region, either upstream or downstream of the coding region. In certain embodiments, the nucleases bind to a target site of 9-20 or more nucleotides within the CISH sequences shown in Table 2.

In another aspect, described herein are compositions comprising one or more of the nucleases (e.g., ZFNs, TALENs, TtAgo and/or CRISPR/Cas systems) described herein, including a nuclease comprising a DNA-binding molecule (e.g., ZFP, TALE, sgRNA, etc.) and a nuclease (cleavage) domain. In certain embodiments, the composition comprises one or more nucleases in combination with a pharmaceutically acceptable excipient. In some embodiments, the composition comprises two or more sets (pairs) of nucleases, each set with different specificities. In other aspects, the composition comprises different types of nucleases. In some embodiments, the composition comprises polynucleotides encoding CISH-nucleases, while in other embodiments, the composition comprises CISH-specific nuclease proteins. In still further embodiments, the composition comprises one or more donor molecules, for example donors that encode a functional CISH protein(s), including any functional fragment thereof. In preferred embodiments, the donor comprises a sequence encoding a chimeric antigen receptor (CAR) and/or other immunomodulatory protein(s) such as an engineered or exogenous T cell receptor (TCR) gene, a gene encoding an ACTR sequence, a beta-2-microglobulin (B2M) gene and/or a fusion protein comprising B2M and an HLA-E and/or HLA-G. In other aspects, the donor comprises a corrective sequence that is integrated into a mutant CISH gene in a cell such that the cell expresses of functional CISH.

In another aspect, described herein is a polynucleotide encoding one or more nucleases or nuclease components (e.g., ZFNs, TALENs, TtAgo or nuclease domains of the CRISPR/Cas system) described herein. The polynucleotide may be, for example, mRNA or DNA. In some aspects, the mRNA may be chemically modified (See e.g. Kormann, et al. (2011) *Nature Biotechnology* 29(2):154-157). In other aspects, the mRNA may comprise an ARCA cap (see U.S. Pat. Nos. 7,074,596; and 8,153,773). In further embodiments, the mRNA may comprise a mixture of unmodified and modified nucleotides (see U.S. Patent Publication No. 2012/0195936). In another aspect, described herein is a nuclease expression vector comprising a polynucleotide, encoding one or more ZFNs, TALENs, TtAgo or CRISPR/

Cas systems described herein, operably linked to a promoter. In one embodiment, the expression vector is a viral vector, for example an AAV vector.

In another aspect, described herein is a host cell comprising one or more nucleases, one or more nuclease expression vectors, and/or one or more donors as described herein. In certain embodiments, the host cell comprises an insertion and/or deletion that inactivates a CISH gene, for example inactivation by NHEJ (indels) following cleavage by the nuclease or inactivation by insertion of one or more exogenous sequences (e.g., transgenes) following cleavage. In certain embodiments, the host cell includes a mutant version of one or more genes (e.g., CISH gene) such that integration of the exogenous sequence mediated by the CISH-specific nuclease provides a functional version of the CISH protein. The host cell may be stably transformed or transiently transfected or a combination thereof with one or more nuclease expression vectors. In one embodiment, the host cell is a T effector cell, a T regulatory cell or a stem cell, for example a hematopoietic stem cell or an induced pluripotent stem cell. In other embodiments, the one or more nuclease expression vectors express one or more nucleases in the host cell. In another embodiment, the host cell may further comprise an exogenous polynucleotide donor sequence (e.g., encoding a CISH protein). In any of the embodiments, described herein, the host cell can comprise an embryo cell, for example a one or more mouse, rat, rabbit or other mammal cell embryo (e.g., a non-human primate). In some embodiments, the host cell comprises a tissue. Also described are cells or cell lines descended from the cells described herein, including pluripotent, totipotent, multipotent or differentiated cells comprising a modification (e.g., integrated donor sequence) in an endogenous CISH gene (e.g., exon 2 or 3 of an endogenous CISH gene). In certain embodiments, described herein are differentiated cells as described herein comprising a modification (e.g., integrated donor sequence) in an endogenous CISH gene (e.g., exon 2 or exon 3 of an endogenous CISH), which differentiated cells are descended from a stem cell as described herein.

In another aspect, described herein is a method for cleaving a CISH gene in a cell, the method comprising: (a) introducing, into the cell, one or more polynucleotides encoding one or more nucleases that target one or more CISH genes under conditions such that the nuclease(s) is(are) expressed and the one or more CISH genes are cleaved. In certain embodiments, following cleavage by the nuclease, a genomic sequence in the target CISH gene is cleaved, for example using a nuclease (or vector encoding the nuclease) as described herein and a "donor" sequence inserted into the gene following targeted cleavage with the ZFN, TALEN, TtAgo or CRISPR/Cas system such that the donor sequence is expressed in the cell. The donor sequence may encode a functional CISH protein. In some embodiments, the donor sequence comprises a partial CISH gene sequence. In preferred embodiments, the donor comprises an immunomodulatory molecule such as a chimeric antigen receptor (CAR). Furthermore, the donor sequence may be present in the nuclease delivery system (e.g., non-viral vector, LNP or viral vector), present in a separate delivery mechanism (e.g., nuclease delivered in mRNA form as naked polynucleotide or via LNP delivery and donor delivered using viral vector such as AAV) or, alternatively, may be introduced into the cell using a separate and/or different nucleic acid delivery mechanism. Insertion of a donor nucleotide sequence into the CISH locus can result in the expression of the transgene under control of the endogenous CISH genetic control elements, respectively. In some aspects, insertion of the transgene of interest results in expression of an intact exogenous protein sequence and lacks any CISH-encoded amino acids. In other aspects, the expressed exogenous protein is a fusion protein and comprises amino acids encoded by the transgene and by the CISH gene. In some instances, the CISH sequences will be present on the amino (N)-terminal portion of the exogenous protein, while in others, the CISH sequences will be present on the carboxy (C)-terminal portion of the exogenous protein. In other instances, CISH sequences will be present on both the N- and C-terminal portions of the exogenous protein. The donor may also be a "corrective" sequence that is integrated into a mutant endogenous CISH gene that does not express the CISH protein (or expresses at levels below normal wild-type levels) such that expression of the CISH is restored.

In some embodiments, the invention describes methods and compositions that can be used to express a transgene under the control of the CISH promoter in vivo. In some aspects, the transgene may encode a therapeutic protein of interest. The transgene may encode a protein such that the methods of the invention can be used for protein replacement. In some aspects, the transgene encodes a protein that modulates T-cell responsiveness and treats and/or prevents a cancer or an immune related condition.

In some embodiments, the nuclease target and/or cleavage site is in an exon of the CISH gene such that a transgene (e.g., CAR, wild-type and engineered TCRs such as ACTRs) is integrated into an exonic region of CISH, for example into exon 2 or exon 3. The transgene may be under the control of another endogenous or exogenous promoter of interest in vivo, ex vivo or in vitro, which exogenous promoter drives expression of the transgene. Thus, the genetically modified cells herein comprising a transgene expressed (from an endogenous or exogenous promoter) can be used in in vitro methods for production of a protein (from the transgene) in a cell culture (which protein can be isolated) or for ex vivo (cell therapy) methods for providing a protein to a subject in need thereof (e.g., a CAR to a subject with cancer or providing a protein that is aberrantly or not expressed in the subject).

In another aspect, a method of modifying an endogenous gene is described, the method comprising administering to the cell one or more polynucleotides encoding one or more nucleases (e.g., ZFNs, TALENs, TtAgo, CRISPR/Cas system) in the presence of one or more donor sequence encoding a CISH protein, such that the donor is integrated into the endogenous gene targeted by the nuclease. Integration of one or more donor molecule(s) occurs via homology-directed repair (HDR) or by non-homologous end joining (NHEJ) associated repair. In certain embodiments, one or more pairs of nucleases are employed, which nucleases may be encoded by the same or different nucleic acids.

In yet another aspect, provided herein is a cell (e.g., T effector cell, T regulatory cell or stem cell) comprising a genetically modified CISH gene. In certain embodiments, a genetically modified cell comprises a genetic modification within exon 2 and/or exon 3 of the CISH gene, for example a modification made by a nuclease. In certain embodiments, the genetically modified CISH gene comprises one or more insertions and/or deletions (known as indels) following cleavage by a nuclease targeted to a target site of 9-20 base pairs of a sequence as shown in Table 2 in the CISH gene wherein the gene is inactivated following cleavage by the nuclease. The genetic modifications may be within the target site(s) and/or cleavage site(s) and/or within 1-50 base pairs of edge of the target site. In other embodiments, the modification comprises insertion of an exogenous sequence, for example a transgene (e.g., CAR, immunomodulating factor, engineered or exogenous TCR or an ACTR etc.), following cleavage by a nuclease as descried herein. In certain embodiments, the cell is made by the methods described herein. In other preferred embodiments, the transgene is integrated into an exon of CISH (e.g., exon 2 or 3, including but not limited into or within 5-10 base pairs of a sequence of 9-20 nucleotides of the sequences as shown in Table 2). The cells comprising the integrated transgene may express the transgene from an endogenous promoter (e.g., the CISH promoter, respectively) or, alternatively, the transgene may include regulatory and control elements such as exogenous promoters that drive expression of the transgene. In certain embodiments, the cells comprising a transgene do not include any viral vector sequences integrated into the genome. The genetically modified cells as described herein can be used for in vitro uses such as protein production (from an integrated transgene) and/or for the provision of cell or animal models with altered CISH genes, including for the screening of molecules for use in treatment of cancer or an inflammatory disease. In addition, the genetically modified cells as described herein can be used for in vivo uses including but not limited to providing a protein to a subject in need thereof via provision of the cell (ex vivo cell therapy).

In any of the methods and compositions described herein, the cells may be any eukaryotic cell. In certain embodiments, the cells are T effector cells, T regulatory cells or stem cells. In other embodiments, the cells are patient-derived, for example autologous CD34+(hematopoietic) stem cells (e.g., mobilized in patients from the bone marrow into the peripheral blood via granulocyte colony-stimulating factor (GCSF) administration). The CD34+ cells can be harvested, purified, cultured, and the nucleases and/or CISH donor (e.g., an adenoviral vector donor) introduced into the cell by any suitable method.

In some aspects, the stem or mature cells may be used for cell therapy, for example, for a T cell transplant using mature cells. In other embodiments, the cells for use in T cell transplant contain another gene modification of interest. In one aspect, the T cells contain an inserted chimeric antigen receptor (CAR) specific for a cancer marker. In a further aspect, the inserted CAR is specific for the CD19 marker characteristic of B cell malignancies. In some embodiments, the T cells comprise a CAR specific for an autoimmune disease. In some embodiments, the T cells are regulatory T cells and comprise a CAR useful for the prevention of transplant rejection.

In another aspect, the methods and compositions of the invention provide for the use of compositions (nucleases, pharmaceutical compositions, polynucleotides, expression vectors, cells, cell lines and/or animals such as transgenic animals) as described herein, for example for use in treatment of a cancer such as B cell malignancies (e.g. B cell acute lymphoblastic leukemia (B-ALL), B cell non-Hodgkin's lymphoma (B-NHL), chronic lymphocytic leukemia (CLL), and Hodgkin's lymphoma (Wang, et al. (2017) *J. Hematol Oncol* 10(1):53) or for the treatment of inflammatory disease (e.g. colitis, see Blat, et al. (2014) *Mol Ther* 22(5):1018-1028). In certain embodiments, these compositions are used in the screening of drug libraries and/or other therapeutic compositions (i.e., antibodies, structural RNAs, etc.) for use in treatment of a cancer or an inflammatory disorder. Such screens can begin at the cellular level with manipulated cell lines or primary cells, and can progress up to the level of treatment of a whole animal (e.g., veterinary or human therapy). Thus, in certain aspects, described herein is a method of treating and/or preventing cancer or an inflammatory in a subject in need thereof, the method comprising administering one or more nucleases, polynucleotides and/or cells as described herein to the subject. The methods may be ex vivo or in vivo. In certain embodiments, a cell as described herein (e.g., a cell comprising a transgene integrated into a CISH gene) is administered to the subject. In any of the methods described herein, the cell may be a stem cell derived from the subject (patient-derived stem cell).

In any of the compositions and methods described herein, the nucleases are introduced in mRNA form and/or using one or more non-viral, LNP or viral vector(s). In certain embodiments, the nuclease(s) are introduced in mRNA form. In other embodiments, the transgene is introduced using a viral vector, for instance an adeno-associated vector (AAV) including AAV1, AAV3, AAV4, AAV5, AAV6, AAV8, AAV 8.2, AAV9, AAV rh10, AAV2/8, AAV2/5 and AAV2/6, or via a lentiviral or integration-defective lentiviral vector, and the nuclease(s) is(are) introduced in mRNA form. In still further embodiments, the nuclease(s) and donors are both introduced using one or more viral or non-viral vectors. The nuclease and donor may be carried on the same vector, on different vectors of the same type or on different vectors of different types. In certain embodiments, the nuclease(s) is(are) introduced in mRNA form (e.g., via electroporation) and the donor is introduced using an AAV (e.g., AAV2/6), lentivirus or integration defective lentivirus. In certain embodiments, the donor is introduced as single-stranded DNA.

The nuclease(s) and donors may be introduced concurrently or in order. When introduced sequentially, any time period (e.g., seconds to hours) may elapse between administration of the nucleases and donors. In certain embodiments, the donors are introduced and after 12-36 hours (or any time therebetween), the nuclease(s) are introduced into the cell. In certain embodiments, the modified cells are incubated for hours to days (or any time therebetween) and then are aliquoted and frozen.

Any cell can be modified using the compositions and methods of the invention, including but not limited to prokaryotic or eukaryotic cells such as bacterial, insect, yeast, fish, mammalian (including non-human mammals), and plant cells. In certain embodiments, the cell is an immune cell, for example a T-cell (e.g., CD4+, CD3+, CD8+, etc.), a dendritic cell, a B cell or the like. In other embodiments, the cell is a pluripotent, totipotent or multipotent stem cell, for example an induced pluripotent stem cell (iPSC), hematopoietic stem cells (e.g., CD34+), an embryonic stem cell or the like. In any of the methods or compositions described herein, the cell containing the CISH-encoding transgene can be a stem or progenitor cell. Specific stem cell types that may be used with the methods and compositions of the invention include embryonic stem cells (ESC), induced pluripotent stem cells (iPSC) and hematopoietic stem cells (e.g., CD34+ cells). The iPSCs can be derived from patient samples and/or from normal controls wherein the patient derived iPSC can be mutated to the normal or wild type gene sequence at the gene of interest, or normal cells can be altered to the known disease allele at the gene of interest. Similarly, the hematopoietic stem cells can be isolated from a patient or from a donor. These cells are then engineered to express functional protein(s) such as CARs, expanded and then reintroduced into the patient. In certain embodiments, the cell is a patient derived hematopoietic stem cell. In other embodiments, the cell is a COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells.

Thus, described herein are methods and compositions for modulating CISH gene expression, including inactivation of CISH with or without expression of an exogenous sequence (such as a CAR). The compositions and methods can be for use in vitro, in vivo or ex vivo, and comprise administering an artificial transcription factor or nuclease that includes a DNA-binding domain targeted to the CISH gene, optionally in the case of a nuclease with a donor that is integrated into the CISH gene following cleavage by the nuclease. In certain embodiments, the cell is in a cancer or an inflammatory disease. In other embodiments, the cell is modified any of the methods described herein, and the modified cell is administered to a subject in need thereof (e.g., a subject with cancer or an inflammatory disorder). Genetically modified cells (e.g., stem cells, precursor cells, T cells, muscle cells, etc.) comprising a genetically modified CISH gene (e.g., an exogenous sequence) are also provided, including cells made by the methods described herein. These cells can be used to provide therapeutic protein(s) to a subject with a cancer or inflammatory disease, for example by administering the cell(s) to a subject in need thereof or, alternatively, by isolating the protein produced by the cell and administering the protein to the subject in need thereof (enzyme replacement therapy).

A kit, comprising the nucleic acids, proteins and/or cells of the invention, is also provided. The kit may comprise nucleic acids encoding the nucleases, (e.g. RNA molecules or ZFN, TALEN, TtAgo or CRISPR/Cas system encoding genes contained in a suitable expression vector), or aliquots of the nuclease proteins, donor molecules, suitable stemness modifiers, cells, instructions for performing the methods of the invention, and the like.

These and other aspects will be readily apparent to the skilled artisan in light of disclosure as a whole.

BRIEF DESCRIPTION OF THE DRAWINGS

FIG. 1 also discloses SEQ ID NO: 50.

FIG. 2A ("Mock") shows results where cells were not treated with the nuclease reagents but otherwise treated in the same way as the other cells. FIG. 2B ("AAV only") shows results where cells received the AAV-GFP donor only. FIG. 2C ("ZFNs only") shows results where cells received only the CISH-targeted nucleases (administered as mRNA); and FIG. 2D ("ZFNs+AAV") shows results where cells were subject to treatment with both the AAV-GFP donor and the CISH-targeted ZFNs. As shown, at least 75% of cells treated with the nucleases and donor expressed GFP as compared to all other treatment conditions in which little (AAV only) or no (mock and ZFNs only) GFP was expressed.

DETAILED DESCRIPTION

Figure 1:
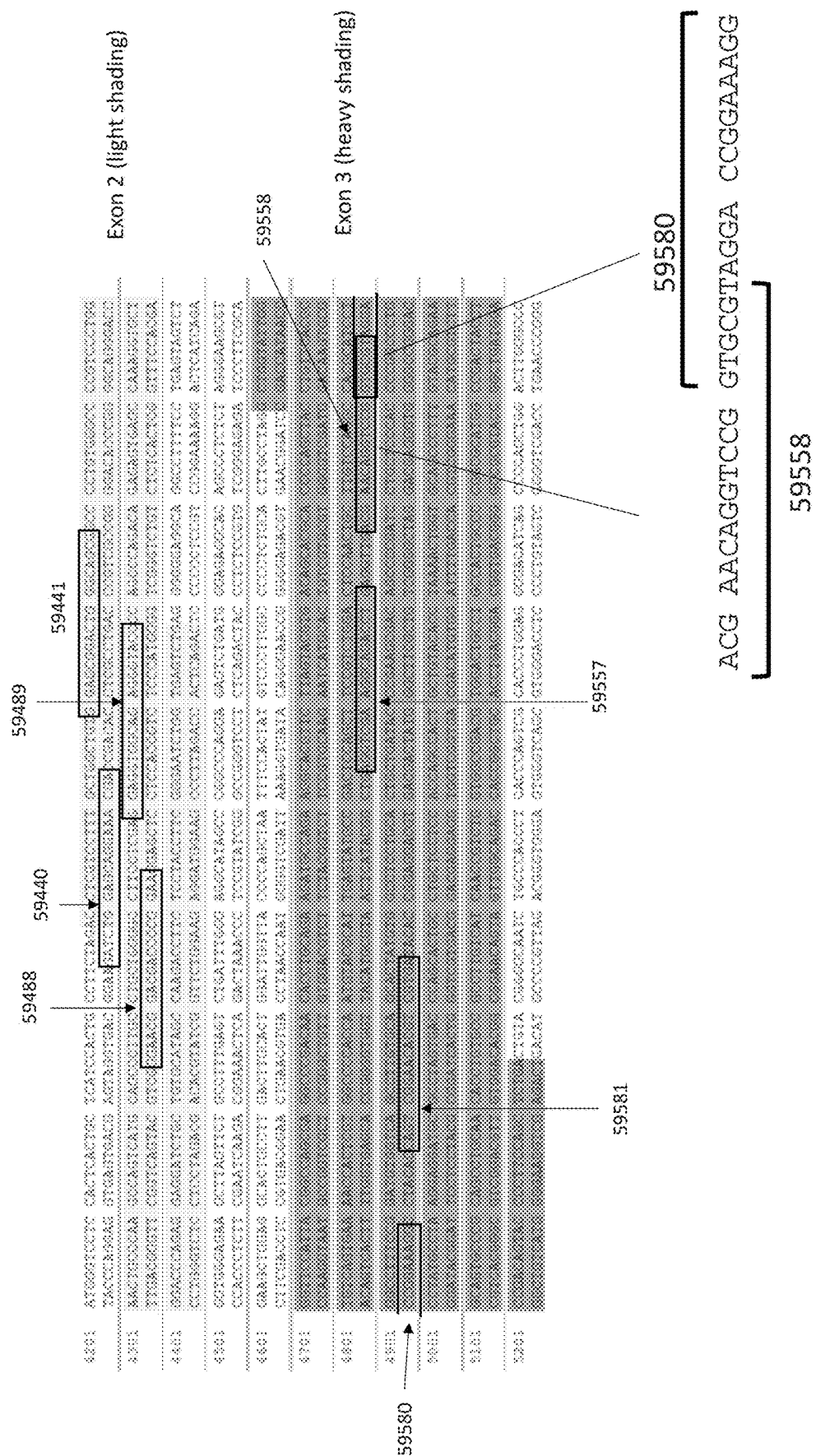
FIG. 1 shows partial sequence including exons 2 and 3 (shaded) of a CISH gene (SEQ ID NO:48) and also shows exemplary nuclease target sites (boxed) in the gene.
Figure 2A:
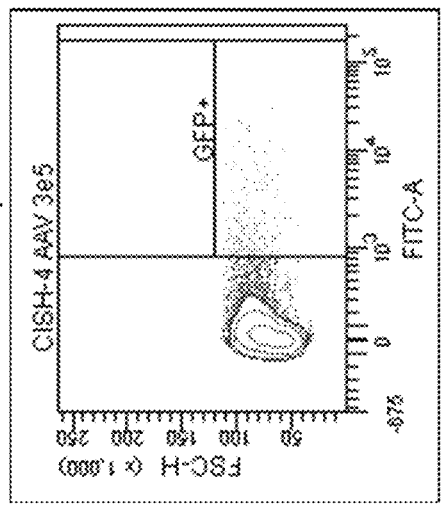
FIGS. 2A through 2D show FACS analysis of T cells subject to treatment under the indicated conditions.
Figure 2B:
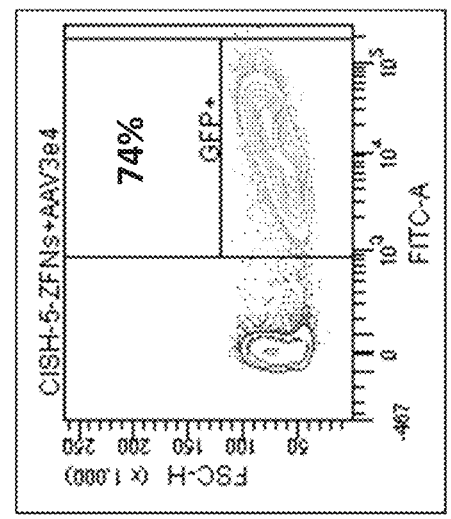
Figure 2C:
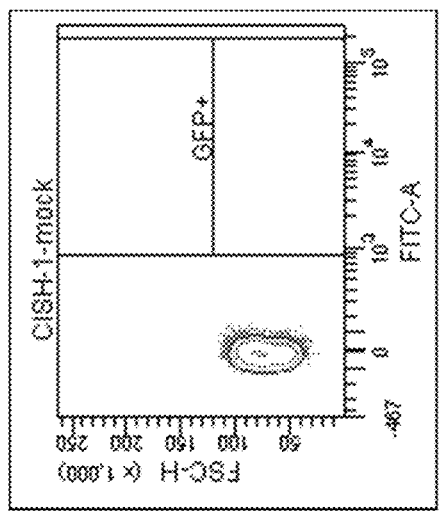
Figure 2D:
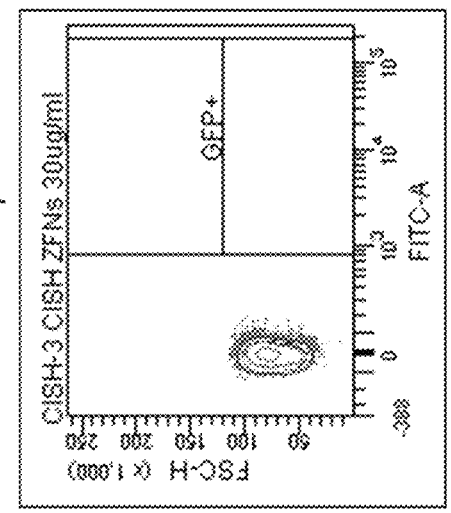

Disclosed herein are compositions and methods for targeted modification of a CISH gene, including modification via integration of a transgene protein (e.g., CAR, TCR, ACTR, and/or any other therapeutic protein) transgene into a CISH gene of cell (e.g., T-cells or lymphocyte precursors such as CD34+ hematopoietic stem cells). The methods and compositions may be used for the modification of a T effector cell (CD4+ or CD8+) and T regulatory cells (CD4+, CD25+,CD127lo, FOXP3+). The cells are suitable for infusion into patients such that subsequent in vivo differentiation of these precursors into cells expressing the functional proteins in the subject with a cancer, inflammatory disorder, autoimmune disease or transplant is provided by the cell, which cells can treat and/or prevent disease in the recipient patient. Genetically modified cells as described herein (e.g., indels and/or transgenes in the CISH gene) are suitable for infusion into patients such that subsequent in vivo differentiation of these stem cells into cells that express the functional CISH protein treat and/or prevent disease (e.g., cancer, inflammatory disorders, etc.) in the patient. In addition, cells as described herein (populations of cells or cell lines) can be used in vitro to produce cells, cell lines or animal models for screening and/or to produce proteins from the integrated transgene, which protein can be isolated and used to treat a subject.

The invention contemplates any genetic modification to a CISH gene, including but not limited to integration of a donor comprising sequence encoding any functional protein, including proteins that treat and/or prevent cancer, inflammatory disorders, autoimmune disease or transplant, or serve as a receptor to redirect a T cell.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook, et al., MOLECULAR CLONING: A LABORATORY MANUAL, Second edition, Cold Spring Harbor Laboratory Press, 1989 and Third edition, 2001; Ausubel, et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding domain" is a molecule that is able to bind non-covalently to another molecule. A binding molecule can bind to, for example, a DNA molecule (a DNA-binding protein such as a zinc finger protein or TAL-effector domain protein or a single guide RNA), an RNA molecule (an RNA-binding protein) and/or a protein molecule (a protein-binding protein). In the case of a protein-binding molecule, it can bind to itself (to form homodimers, homotrimers, etc.) and/or it can bind to one or more molecules of a different protein or proteins. A binding molecule can have more than one type of binding activity. For example, zinc finger proteins have DNA-binding, RNA-binding and protein-binding activity. Thus, DNA-binding molecules, including DNA-binding components of artificial nucleases and transcription factors include but are not limited to, ZFPs, TALEs and sgRNAs.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Artificial nucleases and transcription factors can include a ZFP DNA-binding domain and a functional domain (nuclease domain for a ZFN or transcriptional regulatory domain for ZFP-TF). The term "zinc finger nuclease" includes one ZFN as well as a pair of ZFNs (the members of the pair are referred to as "left and right" or "first and second" or "pair") that dimerize to cleave the target gene.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. Nos. 8,586,526 and 9,458,205. Artificial nucleases and transcription factors can include a TALE DNA-binding domain and a functional domain (nuclease domain for a TALEN or transcriptional regulatory domain for TALEN-TF). The term "TALEN" includes one TALEN as well as a pair of TALENs (the members of the pair are referred to as "left and right" or "first and second" or "pair") that dimerize to cleave the target gene.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261; and 8,585,526; see also International Patent Publication Nos. WO 98/53058; WO 98/53059; WO 98/53060; WO 02/016536; and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 8,586,526; and International Patent Publication Nos. WO 95/19431; WO 96/06166; WO 98/53057; WO 98/54311; WO 00/27878; WO 01/60970; WO 01/88197; and WO 02/099084.

"TtAgo" is a prokaryotic Argonaute protein thought to be involved in gene silencing. TtAgo is derived from the bacteria *Thermus thermophilus*. See, e.g., Swarts, et al., ibid, G. Sheng, et al. (2013) *Proc. Natl. Acad. Sci. U.S.A.* 111, 652. A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break (DSB) in the target sequence (e.g., cellular chromatin) at a predetermined site. The DSB may result in deletions and/or insertions by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins, TALENs, TtAgo or CRISPR/Cas systems can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and −cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 8,623,618; 7,888,121; 7,914,796; and 8,034,598, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. Target sites may be any length, for example, 9 to 20 or more nucleotides and length and the bound nucleotides may be contiguous or non-contiguous.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE, TtAgo or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells), including stem cells (pluripotent and multipotent).

A "T effector cell" (Teff) is a CD4+ or CD8+ T cell that acts immediately to a stimulus. These cells play a central role in cellular-mediated immunity following differentiation. T cells are activated following stimulation by an antigen presenting cell and differentiate into T effector cells that perform critical effector functions such as producing cytotoxic molecules and antibodies. T effector cells migrate to the site of inflammation (e.g. infection) and produce chemokines to recruit additional immune cells.

A "regulatory T cell" (Treg) is also known as a suppressor T cell, and is a subpopulation of T cells that modulate the immune system, maintain tolerance to self-antigens and prevent autoimmune disease. Tregs are immunosuppressive and generally suppress or downregulate induction and proliferation of T effector cells. Tregs are CD4+, CD25+, CD12710 and FOXP3+.

The term "autologous" refers to any material derived from the same individual to whom it is later to be re-introduced.

The term "allogeneic" refers to any material derived from a different individual of the same specie as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE, TtAgo or Cas DNA-binding domain is fused to an activation domain, the ZFP, TALE, TtAgo or Cas DNA-binding domain and the activation domain are in operative linkage if, in the fusion polypeptide, the ZFP, TALE, TtAgo or Cas DNA-binding domain portion is able to bind its target site and/or its binding site, while the activation domain is able to upregulate gene expression. When a fusion polypeptide in which a ZFP, TALE, TtAgo or Cas DNA-binding domain is fused to a cleavage domain, the ZFP, TALE, TtAgo or Cas DNA-binding domain and the cleavage domain are in operative linkage if, in the fusion polypeptide, the ZFP, TALE, TtAgo or Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel, et al., supra. The ability of a protein to interact with another protein can be determined, for example, by co-immunoprecipitation, two-hybrid assays or complementation, both genetic and biochemical. See, for example, Fields, et al. (1989) Nature 340:245-246; U.S. Pat. No. 5,585,245 and International Patent Publication No. WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the nucleases, donors and/or genetically modified cells of the invention can be administered. Subjects of the present invention include those with a disorder.

An "autoimmune disease" is a disease where the immune system is attacking auto-antigens. Examples of an autoimmune disease include discoid lupus erythematosus/lupus erythematosus profundus/chilblain lupus erythematosus/tumidus lupus erythematosus nephropathy, and the chimeric receptor comprises an autoantigen (or a variant or fragment thereof) associated with discoid lupus erythematosus/lupus erythematosus profundus/chilblain lupus erythematosus/tumidus lupus erythematosus nephropathy. Examples of autoantigens associated with discoid lupus erythematosus/lupus erythematosus profundus/chilblain lupus erythematosus/tumidus lupus erythematosus nephropathy include, but are not limited to, ANA.

In one embodiment, the autoimmune disease is Hashimoto's disease, and the chimeric receptor comprises an autoantigen associated with Hashimoto's disease. Examples of autoantigens associated with Hashimoto's disease include, but are not limited to, thyroid peroxidase, and thyroglobulin.

In one embodiment, the autoimmune disease is NMDAR encephalitis, and the chimeric receptor comprises an autoantigen (or a variant or fragment thereof) associated with NMDAR encephalitis. Examples of autoantigens associated with NMDAR encephalitis include, but are not limited to, anti-N-methyl-D-aspartate receptor (NR1 subunit).

In one embodiment, the autoimmune disease is autoimmune hemolytic anemia, and the chimeric receptor comprises an autoantigen (or a variant or fragment thereof) associated with autoimmune hemolytic anemia. Examples of autoantigens associated with autoimmune hemolytic anemia include, but are not limited to, Rh blood group antigens, and I antigen.

In one embodiment, the autoimmune disease is pemphigus vulgaris, and the chimeric receptor comprises an autoantigen (or a variant or fragment thereof) associated with pemphigus vulgaris. Examples of autoantigens associated with pemphigus vulgaris include, but are not limited to, Dsg1/3.

In one embodiment, the autoimmune disease is bullous pemphigoid, and the chimeric receptor comprises an autoantigen (or a variant or fragment thereof) associated with bullous pemphigoid. Examples of autoantigens associated with bullous pemphigoid include, but are not limited to, BP 180, and BP230.

In one embodiment, the autoimmune disease is Myasthenia Gravis, and the chimeric receptor comprises an autoantigen (or a variant or fragment thereof) associated with Myasthenia Gravis. Examples of autoantigens associated with myasthenia gravis include, but are not limited to, acetylcholine nicotinic postsynaptic receptors.

In one embodiment, the autoimmune disease is Graves' disease, and the chimeric receptor comprises an autoantigen (or a variant or fragment thereof) associated with Graves' disease. Examples of autoantigens associated with Graves' disease include but are not limited to, thyrotropin receptors.

In one embodiment, the autoimmune disease is idiopathic thrombocytopenic purpura (ITP), and the chimeric receptor comprises an autoantigen (or a variant or fragment thereof) associated with idiopathic thrombocytopenic purpura (ITP). Examples of autoantigens associated with idiopathic thrombocytopenic purpura include, but are not limited to, Platelet integrin, and GpIIb:IIIa.

In one embodiment, the autoimmune disease is Goodpasture's syndrome, and the chimeric receptor comprises an autoantigen (or a variant or fragment thereof) associated with Goodpasture's syndrome. Examples of autoantigens associated with Goodpasture's syndrome include, but are not limited to, Collagen alpha-3 (IV) chain.

In one embodiment, the autoimmune disease is rheumatoid arthritis, and the chimeric receptor comprises an autoantigen (or a variant or fragment thereof) associated with rheumatoid arthritis. Examples of autoantigens associated with rheumatoid arthritis include, but are not limited to, Rheumatoid factor, and calpastatin.

In one embodiment, the autoimmune disease is juvenile idiopathic arthritis, and the chimeric receptor comprises an autoantigen (or a variant or fragment thereof) associated with juvenile idiopathic arthritis. Examples of autoantigens associated with juvenile idiopathic arthritis include, but are not limited to, RF, citrullinated proteins.

In one embodiment, the autoimmune disease is multiple sclerosis, and the chimeric receptor comprises an autoantigen (or a variant or fragment thereof) associated with multiple sclerosis. Examples of autoantigens associated with multiple sclerosis include, but are not limited to, Myelin basic protein (MBP), Myelin oligodendrocyte glycoprotein (MOG) peptides, and alpha-beta-crystallin.

In one embodiment, the autoimmune disease is celiac disease, and the chimeric receptor comprises an autoantigen (or a variant or fragment thereof) associated with celiac disease. Examples of autoantigens associated with celiac disease include, but are not limited to, tissue transglutaminase (TG2).

In one embodiment, the autoimmune disease is pernicious anemia, and the chimeric receptor comprises an autoantigen (or a variant or fragment thereof) associated with pernicious anemia. Examples of autoantigens associated with pernicious anemia include, but are not limited to, intrinsic factor of gastric parietal cells.

In one embodiment, the autoimmune disease is vitiligo, and the chimeric receptor comprises an autoantigen (or a variant or fragment thereof) associated with vitiligo. Examples of autoantigens associated with vitiligo include, but are not limited to, 65-kDa antigen.

In one embodiment, the autoimmune disease is Behcet's disease, and the chimeric receptor comprises an autoantigen (or a variant or fragment thereof) associated with Behcet's disease. Examples of autoantigens associated with Behcet's disease include, but are not limited to, phosphatidylserine, ribosomal phosphoproteins, and anti-neutrophil cytoplasmic antibody.

In one embodiment, the autoimmune disease is scleroderma, and the chimeric receptor comprises an autoantigen (or a variant or fragment thereof) associated with scleroderma. Examples of autoantigens associated with scleroderma include, but are not limited to, Scl-70, U1-RNP.

In one embodiment, the autoimmune disease is psoriasis, and the chimeric receptor comprises an autoantigen (or a variant or fragment thereof) associated with psoriasis. Examples of autoantigens associated with psoriasis include, but are not limited to, calpastatin.

In one embodiment, the autoimmune disease is ulcerative colitis (UC) and Crohn's disease, and the chimeric receptor comprises an autoantigen (or a variant or fragment thereof) associated with UC and Crohn's disease. Examples of autoantigens associated with UC and Crohn's disease include, but are not limited to, ANA.

In one embodiment, the autoimmune disease is Sjogren's syndrome, and the chimeric receptor comprises an autoantigen (or a variant or fragment thereof) associated with Sjogren's syndrome. Examples of autoantigens associated with Sjogren's syndrome include, but are not limited to, SSA and anti-SSB.

In one embodiment, the autoimmune disease is Wegener's granulomatosis, and the chimeric receptor comprises an autoantigen (or a variant or fragment thereof) associated with Wegener's granulomatosis. Examples of autoantigens associated with Wegener's granulomatosis include, but are not limited to, ANA, and ANCA.

In one embodiment, the autoimmune disease is polymyositis or dermatomyositis, and the chimeric receptor comprises an autoantigen (or a variant or fragment thereof) associated with polymyositis or dermatomyositis. Examples of autoantigens associated with polymyositis or dermatomyositis include, but are not limited to, Jo-1.

In one embodiment, the autoimmune disease is primary biliary cirrhosis, and the chimeric receptor comprises an autoantigen (or a variant or fragment thereof) associated with primary biliary cirrhosis. Examples of autoantigens associated with primary biliary cirrhosis include, but are not limited to, anti-mitochondrial antibodies, gp210, p62, sp 100.

In one embodiment, the autoimmune disease is antiphospholipid syndrome (APS), and the chimeric receptor comprises an autoantigen (or a variant or fragment thereof) associated with antiphospholipid syndrome. Examples of autoantigens associated with antiphospholipid syndrome include, but are not limited to, anti-phospholipid antibodies.

In one embodiment, the autoimmune disease is mixed connective tissue disease (MCTD), and the chimeric receptor comprises an autoantigen (or a variant or fragment thereof) associated with mixed connective tissue disease. Examples of autoantigens associated with mixed connective tissue disease include, but are not limited to, Ul-RNP, Ul-70 kd snRNP.

In one embodiment, the autoimmune disease is Miller Fisher syndrome, and the chimeric receptor comprises an autoantigen (or a variant or fragment thereof) associated with Miller Fisher syndrome. Examples of autoantigens associated with Miller Fisher syndrome include, but are not limited to, GQlb ganglioside.

In one embodiment, the autoimmune disease is Guillain-Barre syndrome, and the chimeric receptor comprises an autoantigen (or a variant or fragment thereof) associated with Guillain-Barre syndrome. Examples of autoantigens associated with Guillain-Barre syndrome include, but are not limited to, GM1, asialo GM1, and GDlb.

In one embodiment, the autoimmune disease is acute motor axonal neuropathy, and the chimeric receptor comprises an autoantigen (or a variant or fragment thereof) associated with acute motor axonal neuropathy. Examples of autoantigens associated with acute motor axonal neuropathy include, but are not limited to, GM1.

In one embodiment, the autoimmune disease is autoimmune hepatitis, and the chimeric receptor comprises an autoantigen (or a variant or fragment thereof) associated with autoimmune hepatitis. Examples of autoantigens associated with autoimmune hepatitis include, but are not limited to, antinuclear antibodies (ANA) and anti-smooth muscle antibodies (ASMA), anti-liver-kidney microsome-1 antibodies (ALKM-1) and anti-liver cytosol antibody-1 (ALC-1).

In one embodiment, the autoimmune disease is dermatitis herpetiformis, and the chimeric receptor comprises an autoantigen (or a variant or fragment thereof) associated with dermatitis herpetiformis. Examples of autoantigens associated with dermatitis herpetiformis include, but are not limited to, IgA anti-endomysial antibodies.

In one embodiment, the autoimmune disease is Churg-Strauss syndrome, and the chimeric receptor comprises an autoantigen (or a variant or fragment thereof) associated with Churg-Strauss syndrome. Examples of autoantigens associated with Churg-Strauss syndrome include, but are not limited to, anti-neutrophil cytoplasm antibodies (ANCAs).

In one embodiment, the autoimmune disease is microscopic polyangiitis, and the chimeric receptor comprises an autoantigen (or a variant or fragment thereof) associated with microscopic polyangiitis. Examples of autoantigens associated with microscopic polyangiitis include, but are not limited to, ANCAs.

In one embodiment, the autoimmune disease is ANCA vasculitis, and the chimeric receptor comprises an autoantigen (or a variant or fragment thereof) associated with ANCA vasculitis. Examples of autoantigens associated with ANCA vasculitis include, but are not limited to, neutrophil granule proteins.

In one embodiment, the autoimmune disease is acute rheumatic fever, and the chimeric receptor comprises an autoantigen (or a variant or fragment thereof) associated with acute rheumatic fever. Examples of autoantigens associated with acute rheumatic fever include, but are not limited to, streptococcal cell wall antigen.

In one embodiment, the autoimmune disease is type 1 Diabetes (TID), and the chimeric receptor comprises an autoantigen (or a variant or fragment thereof) associated with TID. Examples of autoantigens associated with TID include, but are not limited to, insulin (IAA), glutamic acid decarboxylase (GAA or GAD) and protein tyrosine phosphatase (IA2 or ICA512).

In one embodiment, the autoimmune disease is membranous nephropathy, and the chimeric receptor comprises an autoantigen (or a variant or fragment thereof) associated with membranous nephropathy. Examples of autoantigens associated with membranous nephropathy include, but are not limited to, PLA2R1 and THSD7A1.

"Sternness" refers to the relative ability of any cell to act in a stem cell-like manner, i.e., the degree of toti-, pluri-, or oligopotentcy and expanded or indefinite self-renewal that any particular stem cell may have. An "ACTR" is an Antibody-coupled T-cell Receptors that is an engineered T cell component capable of binding to an exogenously supplied antibody. The binding of the antibody to the ACTR component arms the T cell to interact with the antigen recognized by the antibody, and when that antigen is encountered, the ACTR comprising T cell is triggered to interact with antigen (see U.S. Patent Publication No. 2015/0139943).

Fusion Molecules

Described herein are compositions, for example nucleases, that are useful for cleavage of a selected target gene (e.g., CISH) in a cell. In certain embodiments, one or more components of the fusion molecules (e.g., nucleases) are naturally occurring. In other embodiments, one or more of the components of the fusion molecules (e.g., nucleases) are non-naturally occurring, i.e., engineered in the DNA-binding molecules and/or cleavage domain(s). For example, the DNA-binding portion of a naturally-occurring nuclease may be altered to bind to a selected target site (e.g., a single guide RNA of a CRISPR/Cas system or a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains). Thus, any nuclease may be used in the practice of the present invention including but not limited to, at least one ZFN, TALEN, meganuclease, CRISPR/Cas nuclease or the like, which nucleases that cleave a target gene, which cleavage results in genomic modification of the target gene (e.g., insertions and/or deletions into the cleaved gene).

Also described herein are methods to increase specificity of cleavage activity through independent titration of the engineered cleavage half-domain partners of a nuclease complex. In some embodiments, the ratio of the two partners (half cleavage domains) is given at a 1:2, 1:3, 1:4, 1:5, 1:6, 1:8, 1:9, 1:10 or 1:20 ratio, or any value therebetween. In other embodiments, the ratio of the two partners is greater than 1:30. In other embodiments, the two partners are deployed at a ratio that is chosen to be different from 1:1. When used individually or in combination, the methods and compositions of the invention provide surprising and unexpected increases in targeting specificity via reductions in off-target cleavage activity. The nucleases used in these embodiments may comprise ZFNs, TALENs, CRISPR/Cas, CRISPR/dCas and TtAgo, or any combination thereof.

A. DNA-Binding Molecules

The fusion molecules described herein can include any DNA-binding molecule (also referred to as DNA-binding domain), including protein domains and/or polynucleotide DNA-binding domains. In certain embodiments, the DNA-binding domain binds to a sequence comprising 9 to 12 contiguous nucleotides of the sequences shown in Table 2 (SEQ ID NO:40-47).

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG ("LAGLIDADG" disclosed as SEQ ID NO: 49) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032 and 6,833,252; Belfort, et al. (1997) *Nucleic Acids Res.* 25:3379-3388; Dujon, et al. (1989) *Gene* 82:115-118; Perler, et al. (1994) *Nucleic Acids Res.* 22, 1125-1127; Jasin (1996) *Trends Genet.* 12:224-228; Gimble, et al. (1996) *J. Mol. Biol.* 263:163-180; Argast, et al. (1998)*J Mol. Biol.* 280: 345-353 and the New England Biolabs catalogue. In addition, the DNA-binding specificity of homing endonucleases and meganucleases can be engineered to bind non-natural target sites. See, for example, Chevalier, et al. (2002) *Molec. Cell* 10:895-905; Epinat, et al. (2003) *Nucleic Acids Res.* 31:2952-2962; Ashworth, et al. (2006) *Nature* 441:656-659; Paques, et al. (2007) *Current Gene Therapy* 7:49-66; and U.S. Patent Publication No. 2007/0117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay, et al. (2007) *Science* 318:648-651). These proteins contain a DNA binding domain and a transcriptional activation domain. One of the most well characterized TAL-effectors is AvrBs3 from *Xanthomonas campestgris* pv. *vesicatoria* (see Bonas, et al. (1989) *Mol Gen Genet* 218:127-136 and International Patent Publication No. WO 2010/079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al. (2006) *J Plant Physiol* 163(3):256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer, et al. (2007) *Appl and Envir Micro* 73(13):4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas, et al., ibid). Polymorphism of the repeats is usually located at positions 12 and 13 and there appears to be a one-to-one correspondence between the identity of the hypervariable diresidues (RVD) at positions 12 and 13 with the identity of the contiguous nucleotides in the TAL-effector's target sequence (see Moscou and Bogdanove, (2009) *Science* 326:1501 and Boch, et al. (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch, et al., ibid). Engineered TAL proteins have been linked to a FokI cleavage half domain to yield a TAL effector domain nuclease fusion (TALEN). See, e.g., U.S. Pat. No. 8,586,526; Christian, et al. (2010) Genetics 186(2): 757-61 epub 10.1534/genetics.110.120717. In certain embodiments, TALE domain comprises an N-cap and/or C-cap as described in U.S. Pat. No. 8,586,526.

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli, et al. (2002) Nature *Biotechnol.* 20:135-141; Pabo, et al. (2001) *Ann. Rev. Biochem.* 70:313-340; Isalan, et al. (2001) *Nature Biotechnol.* 19:656-660; Segal, et al. (2001) *Curr. Opin. Biotechnol.* 12:632-637; Choo, et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; WO 01/88197; and GB Patent No. 2,338, 237. In addition, enhancement of binding specificity for zinc finger binding domains has been described, for example, in co-owned International Patent Publication No. WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

A ZFP can be operably associated (linked) to one or more nuclease (cleavage) domains to form a ZFN. The term "a ZFN" includes a pair of ZFNs that dimerize to cleave the target gene. Methods and compositions can also be used to increase the specificity of a ZFN, including a nuclease pair, for its intended target relative to other unintended cleavage sites, known as off-target sites (see U.S. Patent Publication No. 20180087072). Thus, nucleases described herein can comprise mutations in one or more of their DNA binding domain backbone regions and/or one or more mutations in their nuclease cleavage domains. These nucleases can include mutations to amino acid within the ZFP DNA binding domain ('ZFP backbone') that can interact non-specifically with phosphates on the DNA backbone, but they do not comprise changes in the DNA recognition helices. Thus, the invention includes mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In preferred embodiments, mutations at made at position (−5), (−9) and/or position (−14) relative to the DNA binding helix. In some embodiments, a zinc finger may comprise one or more mutations at (−5), (−9) and/or (−14). In further embodiments, one or more zinc finger in a multi-finger zinc finger protein may comprise mutations in (−5), (−9) and/or (−14). In some embodiments, the amino acids at (−5), (−9) and/or (−14) (e.g. an arginine (R) or lysine (K)) are mutated to an alanine (A), leucine (L), Ser (S), Asp (N), Glu (E), Tyr (Y) and/or glutamine (Q).

In some aspects, the DNA-binding domain (e.g., ZFP, TALE, sgRNA, etc.) targets a CISH gene. In certain embodiments, the DNA-binding domain targets an exonic region of CISH gene, for example exon 2 or exon 3.

Selection of target sites (e.g., within an intron and/or exon of a CISH gene); ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; and International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding molecule is part of a CRISPR/Cas nuclease system. See, e.g., U.S. Pat. No. 8,697,359 and U.S. Patent Publication No. 2015/0056705. The CRISPR (clustered regularly interspaced short palindromic repeats) locus, which encodes RNA components of the system, and the cas (CRISPR-associated) locus, which encodes proteins (Jansen, et al. (2002) *Mol. Microbiol.* 43:1565-1575; Makarova, et al. (2002) *Nucleic Acids Res.* 30:482-496; Makarova, et al. (2006). *Biol. Direct* 1:7; Haft, et al. (2005) *PLoS Comput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran, et al. (2015) *Nature* 510:186).

In some embodiments, the DNA binding molecule is part of a TtAgo system (see Swarts, et al., ibid; Sheng, et al., ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344:972-973). In contrast, prokaryotic Ago proteins bind to small single-stranded DNA fragments and likely function to detect and remove foreign (often viral) DNA (Yuan, et al. (2005) *Mol. Cell* 19, 405; Olovnikov, et al. (2013) *Mol. Cell* 51:594; Swarts, et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T thermophilus* (TtAgo; Swarts, et al., ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng, et al., ibid). Ago from *Rhodobacter sphaeroides* (RsAgo) has similar properties (Olovnikov, et al., ibid).

Exogenous guide DNAs of arbitrary DNA sequence can be loaded onto the TtAgo protein (Swarts et al., ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celsius. Ago-RNA-mediated DNA cleavage could be used to affect a panoply of outcomes including gene knock-out, targeted gene addition, gene correction, targeted gene deletion using techniques standard in the art for exploitation of DNA breaks.

Thus, the nuclease comprises a DNA-binding molecule in that specifically binds to a target site in any gene into which it is desired to insert a donor (transgene).

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity, including for use in genome modification in a variety of organisms. See, for example, U.S. Pat. Nos. 7,888,121; 8,623,618; 7,888,121; 7,914,796; and 8,034,598; and U.S. Patent Publication No. 2011/0201055. Likewise, TALE DNA-binding domains have been fused to nuclease domains to create TALENs. See, e.g., U.S. Pat. No. 8,586,526.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. Additional enzymes which cleave DNA are known (e.g., S1 Nuclease; mung bean nuclease; pancreatic DNase I; micrococcal nuclease; yeast HO endonuclease. One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150; and 5,487,994; as well as Li, et al. (1992) *Proc. Natl. Acad. Sci. USA* 89:4275-4279; Li, et al. (1993) *Proc. Natl. Acad. Sci. USA* 90:2764-2768; Kim, et al. (1994a) *Proc. Natl. Acad. Sci. USA* 91:883-887; Kim, et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite, et al. (1998) *Proc. Natl. Acad. Sci. USA* 95:10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Publication No. WO 07/014275, incorporated herein in its entirety. Additional restriction enzymes also contain separable binding and cleavage domains, and these are contemplated by the present disclosure. See, for example, Roberts, et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 8,623,618; 7,888,121; 7,914,796; and 8,034,598; and U.S. Patent Publication No. 2011/0201055, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

In certain embodiments, the engineered cleavage half domains are derived from FokI and comprise one or more mutations in one or more of amino acid residues 416, 422, 447, 448, and/or 525 (see, e.g., U.S. Patent Publication No. 2018/0087072) numbered relative to the wild-type full length FokI as shown below:

```
Wild type FokI cleavage half domain
                                      (SEQ ID NO: 1)
QLVKSELEEKKSELRHKLKYVPHEYIELIEIARNSTQDRILEMKVMEFFM

KVYGYRGKHLGGSRKPDGAIYTVGSPIDYGVIVDTKAYSGGYNLPIGQAD

EMQRYVEENQTRNKHINPNEWWKVYPSSVTEFKFLFVSGHFKGNYKAQLT

RLNHITNCNGAVLSVEELLIGGEMIKAGTLTLEEVRRKFNNGEINF
```

These mutations decrease the non-specific interaction between the FokI domain and a DNA molecule. In other embodiments the cleavage half domains derived from FokI comprises a mutation in one or more amino acid residues 414-426, 443-450, 467-488, 501-502, and/or 521-531. The mutations may include mutations to residues found in natural restriction enzymes homologous to FokI. In certain embodiments, the mutations are substitutions, for example substitution of the wild-type residue with a different amino acid, for example serine (S), e.g. R416S or K525S. In a preferred embodiment, the mutation at positions 416, 422, 447, 448 and/or 525 comprise replacement of a positively charged amino acid with an uncharged or a negatively charged amino acid. In another embodiment, the engineered cleavage half domain comprises mutations in amino acid residues 499, 496 and 486 in addition to the mutations in one or more amino acid residues 416, 422, 447, 448, or 525. In a preferred embodiment, the invention provides fusion proteins wherein the engineered cleavage half-domain comprises a polypeptide in which the wild-type Gln (Q) residue at position 486 is replaced with a Glu (E) residue, the wild-type Ile (I) residue at position 499 is replaced with a Leu (L) residue and the wild-type Asn (N) residue at position 496 is replaced with an Asp (D) or a Glu (E) residue ("ELD" or "ELE") in addition to one or more mutations at positions 416, 422, 447, 448, or 525.

Cleavage domains with more than one mutation may be used, for example mutations at positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L;" mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively); engineered cleavage half-domain comprising mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively); and/or engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598; and 8,623,618, the disclosures of which are incorporated by reference in its entirety for all purposes. In other embodiments, the engineered cleavage half domain comprises the "Sharkey" and/or "Sharkey" mutations (see Guo, et al. (2010) *J. Mol. Biol.* 400(1):96-107).

Alternatively, nucleases may be assembled in vivo at the nucleic acid target site using so-called "split-enzyme" technology (see, e.g. U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong, et al. (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek, et al. (2012) *Science* 337: 816-821; Jinek, et al. (2013) *eLife* 2:e00471. DOI: 10.7554/eLife.00471 and Cong, ibid).

In some embodiments, the CRISPR-Cpf1 system is used. The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund, et al. (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "'Cas" includes both Cas9 and Cpf1 proteins. Thus, as used herein, a "CRISPR/Cas system" refers both CRISPR/Cas and/or CRISPR/Cpf1 systems, including both nuclease and/or transcription factor systems.

Target Sites

As described in detail above, DNA-binding domains can be engineered to bind to any sequence of choice. An engineered DNA-binding domain can have a novel binding specificity, compared to a naturally-occurring DNA-binding domain.

In certain embodiments, the nuclease(s) target(s) a CISH gene for example an intron and/or an exon (e.g., exon 2 or 3) of the gene. In certain embodiments, the nuclease binds to a target site of 9-20 or more nucleotides (contiguous or non-contiguous) within a sequence as shown in Table 2.

In certain embodiments, the nuclease target(s) a "safe harbor" loci such as the AAVS1, HPRT, ALB and CCR5 genes in human cells, and Rosa26 in murine cells (see, e.g., U.S. Pat. Nos. 7,888,121; 7,972,854; 7,914,796; 7,951,925; 8,110,379; 8,409,861; 8,586,526; U.S. Patent Publication Nos. 2003/0232410; 2005/0208489; 2005/0026157; 2006/0063231; 2008/0159996; 2010/00218264; 2012/0017290; 2011/0265198; 2013/0137104; 2013/0122591; 2013/0177983; and 2013/0177960) and the Zp15 locus in plants (see U.S. Pat. No. 8,329,986).

Addition non-limiting examples of suitable target genes include a beta (β) globin gene (HBB), a gamma (δ) globin gene (HBG1), a B-cell lymphoma/leukemia 11A (BCL11A) gene, a Kruppel-like factor 1 (KLF1) gene, a CCR5 gene, a CXCR4 gene, a PPP1R12C (AAVS1) gene, an hypoxanthine phosphoribosyltransferase (HPRT) gene, an albumin gene, a Factor VIII gene, a Factor IX gene, a Leucine-rich repeat kinase 2 (LRRK2) gene, a Hungtingin (Htt) gene, a rhodopsin (RHO) gene, a Cystic Fibrosis Transmembrane Conductance Regulator (CFTR) gene, a surfactant protein B gene (SFTPB), a T-cell receptor alpha (TRAC) gene, a T-cell receptor beta (TRBC) gene, a programmed cell death 1 (PD1) gene, a Cytotoxic T-Lymphocyte Antigen 4 (CTLA-4) gene, an human leukocyte antigen (HLA) A gene, an HLA B gene, an HLA C gene, an HLA-DPA gene, an HLA-DQ gene, an HLA-DRA gene, a LMP7 gene, a Transporter associated with Antigen Processing (TAP) 1 gene, a TAP2 gene, a tapasin gene (TAPBP), a class II major histocompatibility complex transactivator (CIITA) gene, a dystrophin gene (DMD), a glucocorticoid receptor gene (GR), a CISH gene, a Rag-1 gene, an RFXS gene, a FAD2 gene, a FAD3 gene, a ZP15 gene, a KASII gene, a MDH gene, and/or an EPSPS gene. In some aspects, the nuclease(s) binds to and/or cleaves a check point inhibitor gene, for example PD-1, CTLA4, receptors for the B7 family of inhibitory ligands, or cleaves a receptor or ligand gene involved in signaling through LAG3, 2B4, BTLA, TIM3, A2aR, and killer inhibitor receptors (KIRs and C-type lectin receptors), see Pardoll (2012) *Nat Rev Cancer* 12(4):252, an HLA complex gene (class I: HLA-A, HLA-B, HLA-C, HLA-E, HLA-F, HLA-G, B2M; class II: HLA-DMA, HLA-DOA, HLA-DPA1, HLA-DQA, HLA-DRA, HLA-DMB, HLA-DOB, HLA-DPB1, HLA-DQB, HLA-DRB) or TCR; and/or a gene encoding a product involved in the peptide loading process and antigen processing for the HLA complexes (e.g. TAP, tapasin, calreticulin, calnexin, LMP2, LMP7 or Erp57). See, e.g., U.S. Pat. Nos. 8,956,828 and 8,945,868.

Donors

In certain embodiments, the present disclosure relates to nuclease-mediated targeted integration of an exogenous sequence (e.g. a transgene encoding a therapeutic protein) into the genome of a cell. As noted above, insertion of an exogenous sequence (also called a "donor sequence" or "donor" or "transgene"), for example for deletion of a specified region and/or correction of a mutant gene or for increased expression of a wild-type gene. It will be readily apparent that the donor sequence is typically not identical to the genomic sequence where it is placed. A donor sequence can contain a non-homologous sequence (e.g., a transgene) flanked by two regions of homology to allow for efficient HDR at the location of interest or can be integrated via non-homology directed repair mechanisms. See, e.g., U.S. Pat. Nos. 9,045,763; 9,005,973; and 7,888,121. Additionally, donor sequences can comprise a vector molecule containing sequences that are not homologous to the region of interest in cellular chromatin. A donor molecule can contain several, discontinuous regions of homology to cellular DNA. Further, for targeted insertion of sequences not normally present in a region of interest, said sequences can be present in a donor nucleic acid molecule and flanked by regions of homology to sequence in the region of interest.

As with nucleases, the donors can be introduced into any form. In certain embodiments, the donors may be introduced using DNA and/or viral vectors by methods known in the art. See, e.g., U.S. Pat. Nos. 9,005,973; 8,936,936; and 8,703,489. The donor may be introduced into the cell in double- or single-stranded form. The donor may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang, et al. (1987) Proc. Natl. Acad. Sci. USA 84:4959-4963; Nehls, et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In certain embodiments, the donor includes sequences (e.g., coding sequences, also referred to as transgenes) greater than 1 kb in length, for example between 2 and 200 kb, between 2 and 10 kb (or any value therebetween). The donor may also include at least one nuclease target site. In certain embodiments, the donor includes at least 2 target sites, for example for a pair of ZFNs, TALENs, TtAgo or CRISPR/Cas nucleases. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor can be inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In some embodiments, the transgene is integrated into the endogenous locus of the CISH gene to correct a mutant version (e.g., in a cell from a patient that is lacking or deficient in a functional version of the CISH gene), for instance, a transgene is integrated into an endogenous CISH gene, for example an exonic (e.g., exon 2 or exon 3) of a CISH gene. In other embodiments, the transgene is integrated into the endogenous locus of a CISH gene such that a functional protein is expressed. Thus, the donor may include any protein-encoding sequences that produce a functional protein, including but not limited to CARs, engineered or exogenous TCRs (see U.S. Pat. No. 8,956,828) and/or ACTRs (U.S. Patent Publication No. 2017/0281682) and combinations thereof.

Furthermore, although not required for expression, exogenous sequences may also include transcriptional or translational regulatory or other sequences, for example, promoters, enhancers, insulators, internal ribosome entry sites, sequences encoding 2A peptides and/or polyadenylation signals. Additionally, splice acceptor sequences may be included.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In some embodiments, the donor further comprises a polynucleotide encoding any polypeptide of which expression in the cell is desired, including, but not limited to antibodies, antigens, enzymes, receptors (cell surface or nuclear or chimeric antigen receptors (CARs)), hormones, lymphokines, cytokines, reporter polypeptides, growth factors, and functional fragments of any of the above. The coding sequences may be, for example, cDNAs.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

In certain embodiments, the transgene may include, for example, wild-type genes to replace mutated endogenous sequences. For example, a wild-type (or other functional) CISH gene sequence may be inserted into the genome of a stem cell in which the endogenous copy of the gene is mutated. The transgene may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Cells

Thus, provided herein are genetically modified cells comprising a genetically modified CISH gene. The genetically modified cells may be modified anywhere within the CISH gene, including non-coding or coding regions, for example within exon 2 and/or exon 3 of the CISH gene. In certain embodiments the modification comprises integration of a transgene that expresses a functional protein in the cell, including cells (e.g., T-cells or stem cells) produced by the methods described herein. The transgene is integrated in a targeted manner into the cell's genome using one or more nucleases. In certain embodiments, the transgene is integrated into a CISH gene, for example in a cancer patient or a patient with an inflammatory disease. The transgene may be integrated into any intronic and/or exonic region of CISH, for example, exon 2 or exon 3. In certain embodiments, the transgene is integrated into or within 5-10 nucleotides on either side of a target site of at least 9 base pairs as shown in Table 2. Thus, provided herein are genetically modified cells comprising a transgene (that expresses a functional protein) integrated in exon 2 or 3 of a CISH gene as well as cells descended from these cells that include the genetic modification.

Unlike random integration, targeted integration ensures that the transgene is integrated into a specified gene. The transgene may be integrated anywhere in the target gene. In certain embodiments, the transgene is integrated at or near the nuclease cleavage site, for example, within 1-300 (or any value therebetween) base pairs upstream or downstream of the site of cleavage, more preferably within 1-100 base pairs (or any value therebetween) of either side of the cleavage site, even more preferably within 1 to 50 base pairs (or any value therebetween) of either side of the cleavage site. In certain embodiments, the integrated sequence comprising the transgene does not include any vector sequences (e.g., viral vector sequences).

Any cell type can be genetically modified as described herein to comprise a transgene, including but not limited to cells and cell lines. Other non-limiting examples of transgene containing cells as described herein include T-cells (e.g., CD4+, CD3+, CD8+, etc.); dendritic cells; B-cells; autologous (e.g., patient-derived) or heterologous pluripotent, totipotent or multipotent stem cells (e.g., CD34+ cells, induced pluripotent stem cells (iPSCs), embryonic stem cells or the like). In certain embodiments, the cells as described herein are CD34+ cells derived from a patient. Cells may be genetically modified in culture or, alternatively, may be genetically modified in vivo by providing the nucleases and/or donors as described herein to the subject.

The cells as described herein are useful in treating and/or preventing cancer or an inflammatory disease in a subject with the disorder, for example, by ex vivo therapies. The nuclease-modified cells can be expanded and then reintroduced into the patient using standard techniques. See, e.g., Tebas, et al. (2014) *New Eng J Med* 370(10):901. In the case of stem cells, after infusion into the subject, in vivo differentiation of these precursors into cells expressing the functional CISH protein also occurs. Pharmaceutical compositions comprising the cells as described herein are also provided. In addition, the cells may be cryopreserved prior to administration to a patient.

The cells and ex vivo methods as described herein provide treatment and/or prevention of a disorder (e.g., cancer or inflammatory disease) in a subject (e.g., a mammalian subject) and eliminate the need for continuous prophylactic pharmaceutical administration or risky procedures such as allogeneic bone marrow transplants or gamma retroviral delivery. As such, the invention described herein provides a safer, cost-effective and time efficient way of treating and/or preventing cancers, inflammatory diseases and other conditions in which immune regulatory is desirable.

Delivery

The nucleases, polynucleotides encoding these nucleases, donor polynucleotides and compositions comprising the proteins and/or polynucleotides described herein may be delivered by any suitable means. In certain embodiments, the nucleases and/or donors are delivered in vivo. In other embodiments, the nucleases and/or donors are delivered to isolated cells (e.g., autologous or heterologous stem cells) for the provision of modified cells useful in ex vivo delivery to patients (cell therapy).

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using any nucleic acid delivery mechanism, including naked DNA and/or RNA (e.g., mRNA) and vectors containing sequences encoding one or more of the components. Any vector systems may be used including, but not limited to, plasmid vectors, DNA minicircles, retroviral vectors, lentiviral vectors, adenovirus vectors, poxvirus vectors; herpesvirus vectors and adeno-associated virus vectors, etc., and combinations thereof. See, also, U.S. Pat. Nos. 6,534,261; 6,607,882; 6,824,978; 6,933,113; 6,979,539; 7,013,219; and 7,163,824; and U.S. Patent Publication No. 2014/0335063, incorporated by reference herein in their entireties. Furthermore, it will be apparent that any of these systems may comprise one or more of the sequences needed for treatment. Thus, when one or more nucleases and a donor construct are introduced into the cell, the nucleases and/or donor polynucleotide may be carried on the same delivery system or on different delivery mechanisms. When multiple systems are used, each delivery mechanism may comprise a sequence encoding one or multiple nucleases and/or donor constructs (e.g., mRNA encoding one or more nucleases and/or mRNA or AAV carrying one or more donor constructs).

Conventional viral and non-viral based gene transfer methods can be used to introduce nucleic acids encoding nucleases and donor constructs in cells (e.g., mammalian cells) and target tissues. Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson (1992) *Science* 256:808-813; Nabel & Felgner (1993) *TIBTECH* 11:211-217; Mitani & Caskey (1993) *TIBTECH* 11:162-166; Dillon (1993) *TIBTECH* 11:167-175; Miller (1992) *Nature* 357:455-460; Van Brunt (1988) *Biotechnology* 6(10):1149-1154; Vigne (1995) *Restorative Neurology and Neuroscience* 8:35-36; Kremer & Perricaudet (1995) *British Medical Bulletin* 51(1):31-44; Haddada, et al., in *Current Topics in Microbiology and Immunology* Doerfler and Bohm (eds.) (1995); and Yu, et al. (1994) *Gene Therapy* 1:13-26.

Methods of non-viral delivery of nucleic acids include electroporation, lipofection, microinjection, biolistics, virosomes, liposomes, immunoliposomes, polycation or lipid:nucleic acid conjugates, lipid nanoparticles (LNP), naked DNA, naked RNA, capped RNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc. (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™) Cationic and neutral lipids that are suitable for efficient receptor-recognition lipofection of polynucleotides include those of Felgner, International Patent Publication Nos. WO 91/17424, WO 91/16024. In some aspects, the nucleases are delivered as mRNAs and the transgene is delivered via other modalities such as viral vectors, minicircle DNA, plasmid DNA, single-stranded DNA, linear DNA, liposomes, nanoparticles and the like.

The preparation of lipid:nucleic acid complexes, including targeted liposomes such as immunolipid complexes, is well known to one of skill in the art (see, e.g., Crystal (1995) *Science* 270:404-410; Blaese, et al. (1995) *Cancer Gene Ther.* 2:291-297; Behr, et al. (1994) *Bioconjugate Chem.* 5:382-389; Remy, et al. (1994) *Bioconjugate Chem.* 5:647-654; Gao, et al. (1995) *Gene Therapy* 2:710-722; Ahmad, et al. (1992) *Cancer Res.* 52:4817-4820; U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al. (2009) *Nature Biotechnology* 27(7):643).

The use of RNA or DNA viral based systems for the delivery of nucleic acids encoding engineered CRISPR/Cas systems take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of CRISPR/Cas systems include, but are not limited to, retroviral, lentiviral, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher, et al. (1992) *J. Virol.* 66:2731-2739; Johann, et al. (1992) *J. Virol.* 66:1635-1640; Sommerfelt, et al. (1990) *Virol.* 176:58-59; Wilson, et al. (1989) *J. Virol.* 63:2374-2378; Miller, et al. (1991) *J. Virol.* 65:2220-2224; International Patent Publication No. WO 1994/026877).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West, et al. (1987) *Virology* 160:38-47; U.S. Pat. No. 4,797,368; International Patent Publication No. WO 93/24641; Kotin (1994) *Human Gene Therapy* 5:793-801; Muzyczka (1994) *J. Clin. Invest.* 94:1351. Construction of recombinant AAV vectors are described in a number of publications, including U.S. Pat. No. 5,173,414; Tratschin, et al. (1985) *Mol. Cell. Biol.* 5:3251-3260; Tratschin, et al. (1984) *Mol. Cell. Biol.* 4:2072-2081; Hermonat & Muzyczka (1984) *PNAS* 81:6466-6470; and Samulski, et al. (1989) *J. Virol.* 63:03822-3828. Any AAV serotype can be used, including AAV1, AAV3, AAV4, AAV5, AAV6 and AAV8, AAV 8.2, AAV9, and AAV rh10 and pseudotyped AAV such as AAV2/8, AAV2/5 and AAV2/6.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar, et al. (1995) *Blood* 85:3048-305; Kohn, et al. (1995) *Nat. Med.* 1:1017-102; Malech, et al. (1997) *PNAS* 94:22 12133-12138). PA317/pLASN was the first therapeutic vector used in a gene therapy trial. (Blaese, et al. (1995) *Science* 270:475-480 (1995)). Transduction efficiencies of 50% or greater have been observed for MFG-S packaged vectors. (Ellem, et al. (1997) *Immunol Immunother.* 44(1):10-20; Dranoff et al. (1997) *Hum. Gene Ther.* 1:111-2.

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair (bp) inverted terminal repeats flanking the transgene expression cassette. Efficient gene transfer and stable transgene delivery due to integration into the genomes of the transduced cell are key features for this vector system. (Wagner, et al. (1998) *Lancet* 351:9117 1702-3; Kearns, et al. (1996) *Gene Ther.* 9:748-55). Other AAV serotypes, including AAV1, AAV3, AAV4, AAV5, AAV6, AAV8, AAV9 and AAVrh10, and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman, et al. (1998) *Hum. Gene Ther.* 7:1083-9). Additional examples of the use of adenovirus vectors for gene transfer in clinical trials include Rosenecker, et al. (1996) *Infection* 24:1 5-10; Sterman, et al. (1998) *Hum. Gene Ther.* 9(7):1083-1089; Welsh, et al. (1995) *Hum. Gene Ther.* 2:205-18; Alvarez, et al. (1997) *Hum. Gene Ther.* 5:597-613; Topf, et al. (1998) *Gene Ther.* 5:507-513; Sterman, et al. (1998) *Hum. Gene Ther.* 7:1083-1089.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han, et al. (1995) *Proc. Natl. Acad. Sci. USA* 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, sublingual or intracranial infusion) topical application, as described below, or via pulmonary inhalation. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application, inhalation and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory, et al. (1996) *Proc. Natl. Acad. Sci. USA* 93:11382-11388; Dull, et al. (1998) *J. Virol.* 72:8463-8471; Zuffery, et al. (1998) *J. Virol.* 72:9873-9880; Follenzi, et al. (2000) *Nature Genetics* 25:217-222; U.S. Pat. No. 8,936,936.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, a donor polynucleotide can be carried by an AAV, while the one or more nucleases can be carried by mRNA. Furthermore, the different systems can be administered by the same or different routes (intramuscular injection, tail vein injection, other intravenous injection, intraperitoneal administration and/or intramuscular injection. Multiple vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods and compositions disclosed herein are for providing therapies for cancers, inflammatory disorders and other diseases, for example via the provision of proteins that modulate T-cell responsiveness. The cell may be modified in vivo or may be modified ex vivo and subsequently administered to a subject. Thus, the methods and compositions provide for the treatment and/or prevention of a disorder.

Targeted integration of a transgene (e.g., CAR transgene, HLA gene, engineered or exogenous TCR gene or ACTR) may be used to correct an aberrant CISH-related gene, insert a wild type gene (e.g., therapeutic proteins), or change the expression of an endogenous gene. For instance, a transgene encoding a CAR may be integrated into a cell to provide a cell that produces a functional CAR protein. Genomic editing may also include correction of mutations (e.g., point mutations) in a faulty endogenous gene, thereby resorting expression of the gene and treating the disorder.

In certain embodiments, one or more CARs are integrated into the CISH gene. CAR transgenes are known in the art and comprise extracellular single chain variable fragment (scFv) with specificity for a particular antigen linked to an intracellular signaling part comprising a costimulatory domain and an activating domain. The costimulatory domain can be derived from, e.g., CD28, and the activating domain can be derived from, e.g., CD3-zeta. CAR transgenes may include two, three, four, or more costimulatory domains. The CAR scFv can be designed to target, for example, CD19, which is a transmembrane protein expressed by cells in the B cell lineage, including all normal B cells and B cell malignances, including but not limited to NHL, CLL, and non-T cell ALL. See, e.g., U.S. Pat. No. 9,855,298. In addition to or instead of the CAR transgene(s), one or more HLA, B2M and/or other immunomodulatory proteins may be integrated into the CISH gene, including but not limited to fusions of B2M and HLA-G and/or HLA-E as described in U.S. patent application Ser. No. 16/058,307 filed Aug. 8, 2018.

By way of non-limiting example, the methods and compositions described herein can be used for treatment and/or prevention of cancers such as B cell leukemias and/or inflammatory diseases such as colitis.

The following Examples relate to exemplary embodiments of the present disclosure in which the nuclease comprises a zinc finger nuclease (ZFN). It will be appreciated that this is for purposes of exemplification only and that other nucleases can be used, for example TALEN, TtAgo and CRISPR/Cas systems, homing endonucleases (meganucleases) with engineered DNA-binding domains and/or fusions of naturally occurring of engineered homing endonucleases (meganucleases) DNA-binding domains and heterologous cleavage domains and/or fusions of meganucleases and TALE proteins. For instance, additional nucleases may be designed to bind to a sequence comprising 9 to 12 contiguous nucleotides of the sequences disclosed herein (e.g., Table 2).

EXAMPLES

Example 1: Zinc Finger Protein Nucleases (ZFN) Targeted to CISH

Zinc finger proteins targeted to CISH were designed and incorporated into mRNA, plasmids, AAV or adenoviral vectors essentially as described in Urnov, et al. (2005) *Nature* 435(7042):646-651, Perez, et al. (2008) *Nature Biotechnology* 26(7):808-816, and as described in U.S. Pat. No. 6,534,261. Table 1 shows the recognition helices within the DNA binding domain of exemplary CISH ZFP DNA-binding domains and the target sites for these ZFPs (DNA target sites indicated in uppercase letters; non-contacted nucleotides indicated in lowercase). Nucleotides in the target site that are contacted by the ZFP recognition helices are indicated in uppercase letters; non-contacted nucleotides indicated in lowercase. TALENs and/or sgRNAs are also designed to the CISH sequences shown in Table 2 (e.g., a target site comprising 9 to 20 or more (including 9, 10, 11, 12, 13, 14, 15, 16, 17, 18, 19, 20, 21, or more) nucleotides (contiguous or non-contiguous) of the target sites shown in Table 2 following methods known in the art. See, e.g., U.S. Pat. No. 8,586,526 (using canonical or non-canonical RVDs for TALENs) and U.S. Patent Publication No. 2015/0056705.

TABLE 1

CISH Zinc finger proteins recognition helix designs

| SBS # | Linker | Design | | | | | |
|---|---|---|---|---|---|---|---|
| | | F1 | F2 | F3 | F4 | F5 | F6 |
| 59488 | L0 | RSDHLSQ (SEQ ID NO: 2) | QNATRTK (SEQ ID NO: 3) | RSDNLSE (SEQ ID NO: 4) | KRCNLRC (SEQ D NO: 5) | DRSTRTK (SEQ ID NO: 6) | RRDNLHS (SEQ ID NO: 7) |
| 59489 | L0 | GHTSLKR (SEQ ID NO: 8) | TSGHLSR (SEQ ID NO: 9) | RSDNLAR (SEQ ID NO: 10) | QNVSRPR (SEQ ID NO: 11) | TSGHLSR (SEQ ID NO: 9) | QSGHLSR (SEQ ID NO: 12) |
| 59440 | L0 | RWQYLPT (SEQ ID NO: 13) | DRSALAR (SEQ ID NO: 14) | RSDNLAR (SEQ ID NO: 10) | DRSNLTR (SEQ ID NO: 15) | QSGNLAR (SEQ ID NO: 16) | ATCCLAH (SEQ ID NO: 17) |
| 59441 | L0 | RSDDLTR (SEQ ID NO: 18) | QAATLSR (SEQ ID NO: 19) | RSDHLSA (SEQ ID NO: 20) | DRSDLSR (SEQ ID NO: 21) | RSDDLTR (SEQ ID NO: 18) | DRSHLAR (SEQ ID NO: 22) |
| 59558 | N6a | QSGDLTR (SEQ ID NO: 23) | QSGNLHV (SEQ ID NO: 24) | QSGHLAR (SEQ ID NO: 25) | NRYDLMT (SEQ ID NO: 26) | RSDSLLR (SEQ ID NO: 27) | CREYRGK (SEQ ID NO: 28) |

TABLE 1 -continued

CISH Zinc finger proteins recognition helix designs

| SBS # | Linker | F1 | F2 | F3 | F4 | F5 | F6 |
|---|---|---|---|---|---|---|---|
| 59557 | L0 | QSSHLTR (SEQ ID NO: 29) | QSSDLTR (SEQ ID NO: 30) | QSGNLAR (SEQ ID NO: 16) | RLDILQQ (SEQ ID NO: 31) | RSDNLST (SEQ ID NO: 32) | DNSYLPR (SEQ ID NO: 33) |
| 59581 | N7a | DRSNLSR (SEQ ID NO: 34) | LRQDLKR (SEQ ID NO: 35) | RSDNLST (SEQ ID NO: 32) | DNSNRIN (SEQ ID NO: 36) | QSSDLSR (SEQ ID NO: 37) | WKWNLRA (SEQ ID NO: 38) |
| 59580 | L0 | RSDSLLR (SEQ ID NO: 27) | CREYRGK (SEQ ID NO: 28) | QSGHLAR (SEQ ID NO: 25) | QKGTLGE (SEQ ID NO: 39) | RSDNLST (SEQ ID NO: 32) | QSGHLSR (SEQ ID NO: 12) |

TABLE 2

Target Sites of zinc finger proteins

| SBS # | Target site |
|---|---|
| 59488 | 5' ggAAGGCCcCAGCAGGCAAGGgctgcat (SEQ ID NO: 40) |
| 59489 | 5' gaGGAGGT9GCAGAGGGTACCccagccc (SEQ ID NO: 41) |
| 59440 | 5' ccAGCAAAgGACGAGGTCTAGaaggcag (SEQ ID NO: 42) |
| 59441 | 5' gtGGAGCGGACTGGGCAGCGgcccctgt (SEQ ID NO: 43) |
| 59558 | 5' gaTGCGTGgCCTGGACAAGCAgttggag (SEQ ID NO: 44) |
| 59557 | 5' gaGTCCAGACGGAAGCTGGAgtcggcat (SEQ ID NO: 45) |
| 59581 | 5' atAGTGCTgCACAAGGCTGACcacatcc (SEQ ID NO: 46) |
| 59580 | 5' ccGGAAAGgCCAGGATGCGTGgcctgga (SEQ ID NO: 47) |

All ZFN pairwise combinations were tested for cleavage activity Activated T cells were electroporated with mRNAs encoding CISH targeting ZFNs over a range of mRNA (0.5 µg to 6 µg per 3E6 T cell in a 100 uL transfection reaction). T cells were expanded for 3-4 days post transfection, genomic DNA were harvested and CISH editing efficiency is assessed by deep sequencing. All pairs were found to be active as shown in Table 3 (where the percent cleavage is shown with the indicated pairs at the indicated dosage, for example 89% cleavage of the CISH gene using pair 59488/59489 using 6 µg mRNA).

TABLE 3

Nuclease-mediated cleavage

| | ZFN pairs | | 6 µg | 2 µg | 0.5 µg |
|---|---|---|---|---|---|
| Exon 2 | 59488 | 59489 | 89 | 84 | 60 |
| | 59440 | 59441 | 84 | 82 | 59 |
| Exon 3 | 59558 | 59557 | 84 | 80 | 55 |
| | 59581 | 59580 | 82 | 83 | 72 |

It will be apparent that these designs may include any linker between any of the finger modules and/or between the ZFP and the cleavage domain, including but not limited to canonical or non-canonical linkers (between fingers) and/or linkers between the ZFP and cleavage domain as described in U.S. Pat. No. 9,394,531. See, also, U.S. Pat. No. 8,772,453 and U.S. Patent Publication No. 2015/0064789.

Furthermore, any of the nucleases (ZFNs, CRISPR/Cas systems and TALENs) can include engineered cleavage domains, for example heterodimers disclosed in U.S. Pat. No. 8,623,618 (e.g., ELD and KKR engineered cleavage domains) and/or cleavage domains with more or more mutations in positions 416, 422, 447, 448, and/or 525 as described in U.S. Patent Publication No. 2018/0087072. ZFNs may also include one or more mutations in the backbone residues of the ZFP as described in U.S. Patent Publication No. 2018/0087072. These mutants were used in conjunction with the exemplary DNA-binding domains described herein.

Example 2: Targeted CISH Donor Insertion

Targeted integration into the CISH locus was also performed using an AAV GFP donor. First, an AAV GFP donor was constructed to encode a GFP expression cassette that is flanked by homology arms 5' and 3' to the CISH cleavage site. When cells are treated with the CISH targeted ZFN and co-administer with the AAV donor, the flanking homology arms are necessary to mediate targeted insertion of the GFP expression cassette into the CISH cleavage site via the homology directed repair pathway. In this experiment, activated T cells are electroporated with CISH mRNA, and co-administer with the AAV GFP donor. Targeted integration efficiency was assessed 7 days later by FACS analysis of % GFP positive cells.

Figure 3:
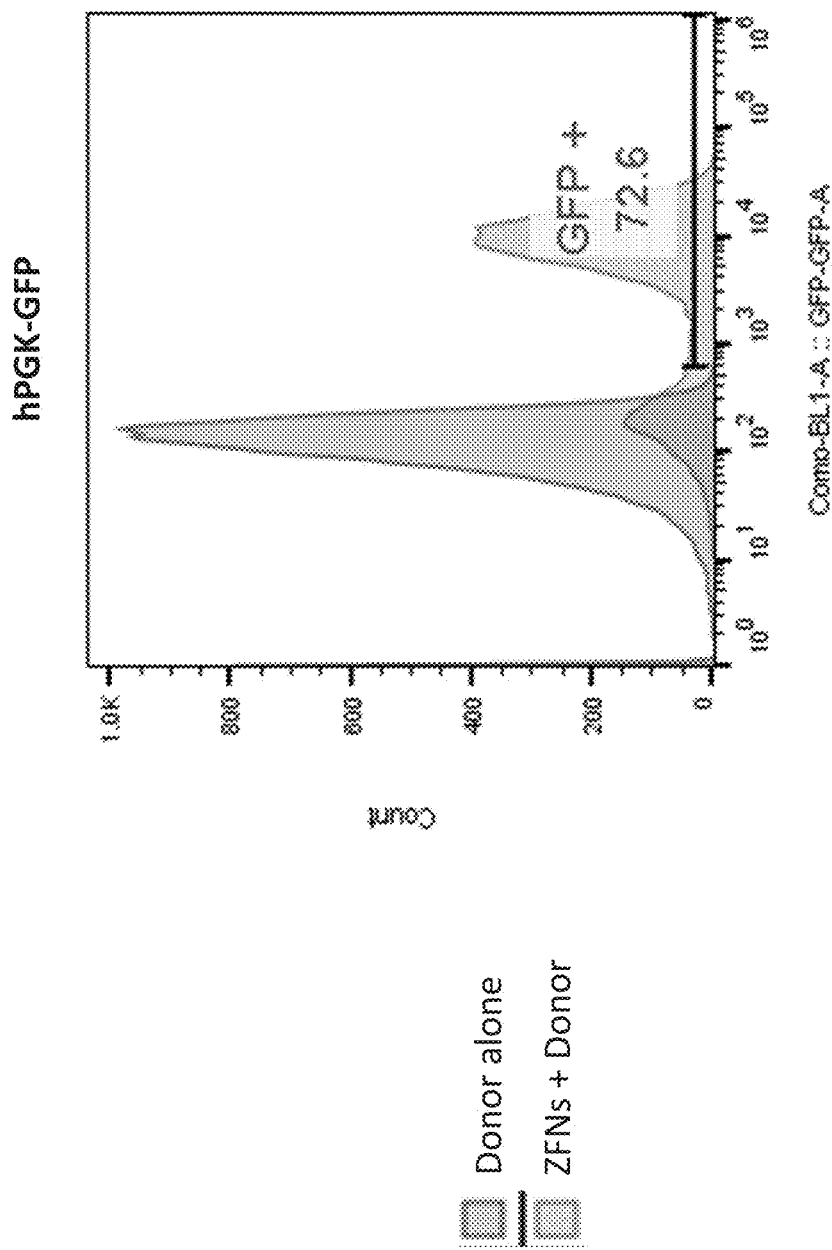
FIG. 3 show FACS analysis of effector T cells subject to treatment under the indicated conditions. "Donor alone" refers to cells which received the AAV-hPGK-GFP only and "ZFNs+Donor" refer to cells subject to treatment with both the AAV-hPGK-GFP donor and the CISH-targeted ZFNs. As shown, —72.6% of cells treated with the nucleases and donor expressed GFP as compared to the cells treated with AAV donor alone which did not express any GFP.
Figure 4:
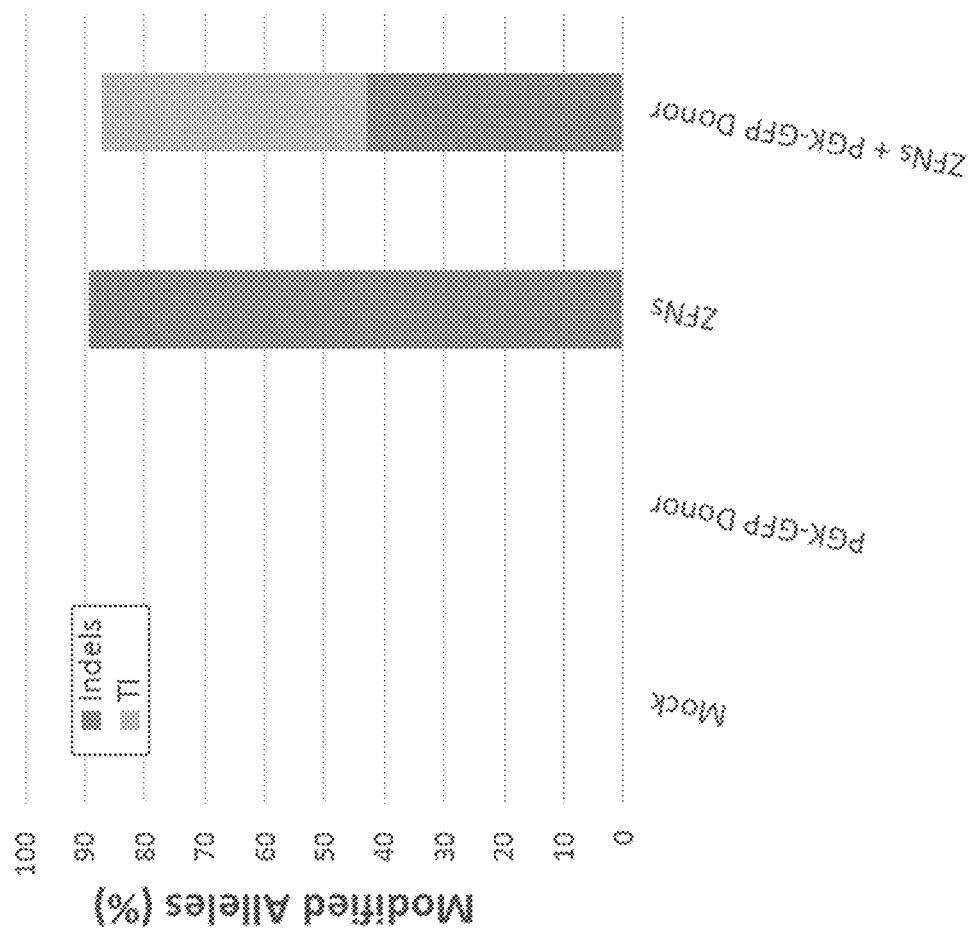
FIG. 4 is a graph showing results of Miseq genotype analysis of effector T cells subject to treatment under the indicated conditions. "Mock" refers to cells that were not treated with the nuclease reagents but otherwise treated in the same way as the other cells; "PGK-GFP Donor" refers to cells which received the AAV-hPGK-GFP donor only; "ZFNs" refer to cells to which only the CISH-targeted nucleases were administered as mRNA; and "ZFNs+PGK-GFP Donor" refer to cells subject to treatment with both the AAV-hPGK-GFP donor and the CISH-targeted ZFNs. As shown, ~90% of alleles are modified in cells treated with the nucleases (ZFNs and ZFNs+Donor), whereas only cells treated with both the AAV donor and ZFNs yielded high levels (~45%) of targeted integration (TI) of the donor. The group treated with AAV donor alone or Mock had no detectable levels of genome modification.

As shown in FIGS. 2 and 3, FACS analysis for GFP expression showed that at least 70% efficiency of donor (GFP) insertion was obtained in cells receiving both CISH targeted nucleases as described herein and the donor.

Example 3: Enhanced Immunostimulatory Activation Following Donor Insertion at CISH Compared to AAVS1 Safe Harbor Locus Targeted integration into the CISH or AAVS1 locus was also performed using an AAV GFP donor. First, an AAV GFP donor was constructed to encode a GFP expression cassette that is flanked by homology arms 5' and 3' to the CISH or AAVS1 cleavage site. When cells are treated with the CISH or AAVS1 targeted ZFNs (CISH-specific ZFNs: SB59440/

SB59441 (as shown in Table 1 above); AAVS1-specific ZFNs (comprising ZFPs designated SB30054 and SB30035 as described in U.S. Pat. No. 9,957,526) and co-administered with the corresponding AAV donor, the flanking homology arms are necessary to mediate targeted insertion of the GFP expression cassette into the CISH or AAVS1 cleavage site via the homology directed repair pathway. In this experiment, activated effector T cells are electroporated with CISH or AAVS1 ZFN mRNA, and co-administer with the corresponding AAV GFP donor. Genome modification efficient was assessed 7 days later by Miseq analysis.

Figure 5:
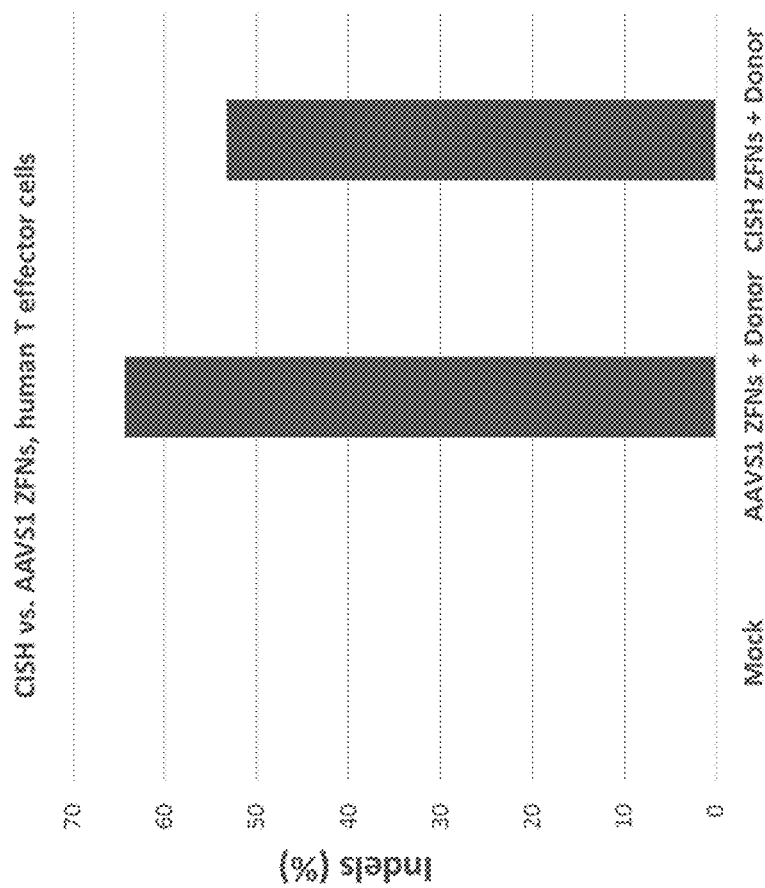
FIG. 5 is a graph showing Miseq genotype analysis of effector T cells subject to treatment under the indicated conditions. "Mock" refers to cells that were not treated with the nuclease reagents but otherwise treated in the same way as the other cells and "ZFNs+Donor" refers to cells subject to treatment with either AAVS1 or CISH-targeted ZFNs along with a corresponding AAV-GFP donor. As shown, ~50-60% of alleles are modified in cells treated with the nucleases (ZFNs+Donor), whereas the Mock group had no detectable levels of genome modification.
Figure 6:
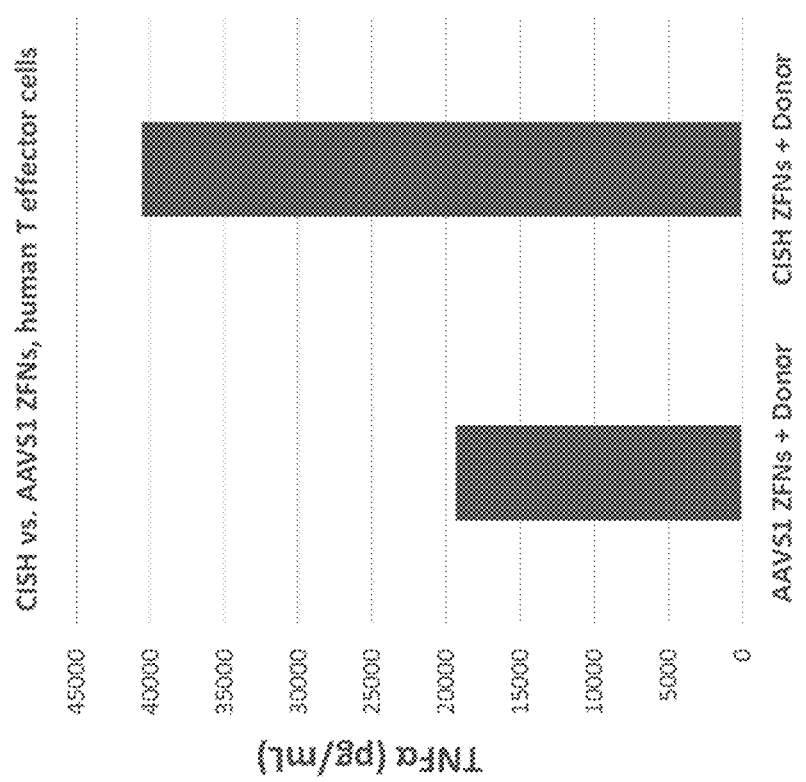
FIG. 6 is a graph showing effector T cell functional data as assessed by immunostimulatory cytokine secretion via Luminex analysis. "ZFNs+Donor" refers to cells subject to treatment with either AAVS1 or CISH-targeted ZFNs along with a corresponding AAV-GFP donor. As shown TI of a transgene donor into CISH results in increased immunostimulatory function (i.e. TNFα upregulation) of the effector T cells as compared with TI into the genomic safe harbor locus AAVS1, presumably due to knockout of CISH expression in a large fraction of cells.

As shown in FIG. 5, high levels of genome modification efficiency was obtained in cells receiving both CISH or AAVS1 targeted nucleases as described herein and the AAV GFP donor. FIG. 6 demonstrates that targeted integration of the GFP donor at CISH enhances effector T cell immunostimulatory function upon TCR-mediated activation, presumably due to knockout of CISH, a member of the suppressor of cytokine signaling (SOCS) family, expression.

Example 4: Ex Vivo Methods

The genetically modified cells (e.g., T-cells or hematopoietic stem cells) as described herein, comprising a transgene integrated into the CISH gene (e.g., a CAR and/or other therapeutic transgene) are administered to patients with a cancer or an inflammatory disorder. Administration (single or multiple dosing) of the cells is any method known in cell therapy. The disease or disorder (or symptoms thereof) is ameliorated following administration.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A genetically modified eukaryotic cell comprising a genomic modification within exon 2 or exon 3 of an endogenous Cytokine Inducible SH2-containing protein (CISH) gene wherein the CISH gene is modified within exon 2 or exon 3 by one or more insertions, deletions, or combinations thereof following cleavage by a zinc finger nuclease, wherein the zinc finger nuclease comprises a zinc finger protein comprising 6 zinc finger domains each comprising a recognition helix region designated SBS #59488, SBS #59489, SBS #59440, SBS #59441, SBS #59558, SBS #59557, SBS #59581 or SBS #59580, wherein the recognition helix regions F1 to F6 are in the order of F1 to F6 as shown in a single row of the table below:

|  | Design | | |
|---|---|---|---|
| SBS # | F1 | F2 | F3 |
| 59488 | RSDHLSQ (SEQ ID NO: 2) | QNATRTK (SEQ ID NO: 3) | RSDNLSE (SEQ ID NO: 4) |
| 59489 | GHTSLKR (SEQ ID NO: 8) | TSGHLSR (SEQ ID NO: 9) | RSDNLAR (SEQ ID NO: 10) |
| 59440 | RWQYLPT (SEQ ID NO: 13) | DRSALAR (SEQ ID NO: 14) | RSDNLAR (SEQ ID NO: 10) |
| 59441 | RSDDLTR (SEQ ID NO: 18) | QAATLSR (SEQ ID NO: 19) | RSDHLSA (SEQ ID NO: 20) |
| 59558 | QSGDLTR (SEQ ID NO: 23) | QSGNLHV (SEQ ID NO: 24) | QSGHLAR (SEQ ID NO: 25) |
| 59557 | QSSHLTR (SEQ ID NO: 29) | QSSDLTR (SEQ ID NO: 30) | QSGNLAR (SEQ ID NO: 16) |
| 59581 | DRSNLSR (SEQ ID NO: 34) | LRQDLKR (SEQ ID NO: 35) | RSDNLST (SEQ ID NO: 32) |
| 59580 | RSDSLLR (SEQ ID NO: 27) | CREYRGK (SEQ ID NO: 28) | QSGHLAR (SEQ ID NO: 25) |

|  | Design | | |
|---|---|---|---|
| SBS # | F4 | F5 | F6 |
| 59488 | KRCNLRC (SEQ ID NO: 5) | DRSTRTK (SEQ ID NO: 6) | RRDNLHS (SEQ ID NO: 7) |
| 59489 | QNVSRPR (SEQ ID NO: 11) | TSGHLSR (SEQ ID NO: 9) | QSGHLSR (SEQ ID NO: 12) |
| 59440 | DRSNLTR (SEQ ID NO: 15) | QSGNLAR (SEQ ID NO: 16) | ATCGLAH (SEQ ID NO: 17) |
| 59441 | DRSDLSR (SEQ ID NO: 21) | RSDDLTR (SEQ ID NO: 18) | DRSHLAR (SEQ ID NO: 22) |
| 59558 | NRYDLMT (SEQ ID NO: 26) | RSDSLLR (SEQ ID NO: 27) | CREYRGK (SEQ ID NO: 28) |
| 59557 | RLDILQQ (SEQ ID NO: 31) | RSDNLST (SEQ ID NO: 32) | DNSYLPR (SEQ ID NO: 33) |
| 59581 | DNSNRIN (SEQ ID NO: 36) | QSSDLSR (SEQ ID NO: 37) | WKWNLRA (SEQ ID NO: 38) |
| 59580 | QKGTLGE (SEQ ID NO: 39) | RSDNLST (SEQ ID NO: 32) | QSGHLSR (SEQ ID NO: 12) |

2. The genetically modified eukaryotic cell of claim 1, wherein one or more transgenes is/are integrated into the CISH gene.

3. The genetically modified eukaryotic cell of claim 2, wherein the transgene encodes a chimeric antigen receptor (CAR), an immunomodulating factor, an engineered or exogenous T cell receptor (TCR).

4. The genetically modified eukaryotic cell of claim 3, wherein the engineered TCR is an antibody-coupled T-cell receptors (ACTR).

5. The genetically modified eukaryotic cell of claim 1, wherein the zinc finger nuclease comprises a DNA-binding domain that binds to a target site as shown below:

```
SBS #Target site
59488 5' ggAAGGCCcCAGCAGGCAAGGgctgcat
      (SEQ ID NO: 40)
59489 5' gaGGAGGTgGCAGAGGGTACCccagccc
      (SEQ ID NO: 41)
59440 5' ccAGCAAAgGACGAGGTCTAGaaggcag
      (SEQ ID NO: 42)
59441 5' gtGGAGCGGACTGGGCAGCGgccctgt
      (SEQ ID NO: 43)
59558 5' gaTGCGTGgCCTGGACAAGCAgttggag
      (SEQ ID NO: 44)
59557 5' gaGTCCAGACGGAAGCTGGAgtcggcat
      (SEQ ID NO: 45)
59581 5' atAGTGCTgCACAAGGCTGACcacatcc
      (SEQ ID NO: 46)
59580 5' ccGGAAAGgCCAGGATGCGTGgcctgga
      (SEQ ID NO: 47).
```

6. The genetically modified eukaryotic cell of claim 1 or a cell descended therefrom, wherein the cell is selected from the group consisting of a hematopoietic stem cell, a T effector cell and a T regulatory cell.

7. A method of generating a genetically modified eukaryotic cell according to claim 1, the method comprising introducing, into the cell, one or more polynucleotides encoding one or more zinc finger nuclease comprising a DNA-binding domain that binds to target site in exon 2 or exon 3 of the CISH gene, wherein the zinc finger nuclease comprises a zinc finger protein comprising 6 zinc finger domains each comprising a recognition helix region, wherein the zinc finger protein comprises the recognition helix regions designated SBS #59488, SBS #59489, SBS #59440, SBS #59441, SBS #59558, SBS #59557, SBS #59581 or SBS #59580, wherein the recognition helix regions F1 to F6 are in the order of F1 to F6 as shown in a single row of the table below:

|  | Design | | |
|---|---|---|---|
| SBS # | F1 | F2 | F3 |
| 59488 | RSDHLSQ (SEQ ID NO: 2) | QNATRTK (SEQ ID NO: 3) | RSDNLSE (SEQ ID NO: 4) |
| 59489 | GHTSLKR (SEQ ID NO: 8) | TSGHLSR (SEQ ID NO: 9) | RSDNLAR (SEQ ID NO: 10) |
| 59440 | RWQYLPT (SEQ ID NO: 13) | DRSALAR (SEQ ID NO: 14) | RSDNLAR (SEQ ID NO: 10) |
| 59441 | RSDDLTR (SEQ ID NO: 18) | QAATLSR (SEQ ID NO: 19) | RSDHLSA (SEQ ID NO: 20) |
| 59558 | QSGDLTR (SEQ ID NO: 23) | QSGNLHV (SEQ ID NO: 24) | QSGHLAR (SEQ ID NO: 25) |
| 59557 | QSSHLTR (SEQ ID NO: 29) | QSSDLTR (SEQ ID NO: 30) | QSGNLAR (SEQ ID NO: 16) |

-continued

| SBS # | | | |
|---|---|---|---|
| 59581 | DRSNLSR (SEQ ID NO: 34) | LRQDLKR (SEQ ID NO: 35) | RSDNLST (SEQ ID NO: 32) |
| 59580 | RSDSLLR (SEQ ID NO: 27) | CREYRGK (SEQ ID NO: 28) | QSGHLAR (SEQ ID NO: 25) |

| | Design | | |
|---|---|---|---|
| SBS # | F4 | F5 | F6 |
| 59488 | KRCNLRC (SEQ ID NO: 5) | DRSTRTK (SEQ ID NO: 6) | RRDNLHS (SEQ ID NO: 7) |
| 59489 | QNVSRPR (SEQ ID NO: 11) | TSGHLSR (SEQ ID NO: 9) | QSGHLSR (SEQ ID NO: 12) |
| 59440 | DRSNLTR (SEQ ID NO: 15) | QSGNLAR (SEQ ID NO: 16) | ATCGLAH (SEQ ID NO: 17) |
| 59441 | DRSDLSR (SEQ ID NO: 21) | RSDDLTR (SEQ ID NO: 18) | DRSHLAR (SEQ ID NO: 22) |

-continued

| SBS # | | | |
|---|---|---|---|
| 59558 | NRYDLMT (SEQ ID NO: 26) | RSDSLLR (SEQ ID NO: 27) | CREYRGK (SEQ ID NO: 28) |
| 59557 | RLDILQQ (SEQ ID NO: 31) | RSDNLST (SEQ ID NO: 32) | DNSYLPR (SEQ ID NO: 33) |
| 59581 | DNSNRIN (SEQ ID NO: 36) | QSSDLSR (SEQ ID NO: 37) | WKWNLRA (SEQ ID NO: 38) |
| 59580 | QKGTLGE (SEQ ID NO: 39) | RSDNLST (SEQ ID NO: 32) | QSGHLSR (SEQ ID NO: 12) | and wherein the nuclease bind to and cleave the CISH gene, thereby genetically modifying the cell.

8. The method of claim 7, wherein the genetically modified eukaryotic cell comprises a transgene that is integrated into the CISH gene and expressed in the cell.

9. A method of providing a protein to a subject in need thereof, the method comprising administering a genetically modified eukaryotic cell according to claim 2 wherein the cell expresses the transgene in the subject.

\* \* \* \* \*

SEQUENCE LISTING

```
<160> NUMBER OF SEQ ID NOS: 50

<210> SEQ ID NO 1
<211> LENGTH: 196
<212> TYPE: PRT
<213> ORGANISM: Unknown
<220> FEATURE:
<223> OTHER INFORMATION: Description of Unknown:
      FokI cleavage half domain sequence

<400> SEQUENCE: 1

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 2
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ser Asp His Leu Ser Gln
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Asn Ala Thr Arg Thr Lys
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Asp Asn Leu Ser Glu
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Arg Cys Asn Leu Arg Cys
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Arg Ser Thr Arg Thr Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7
```

Arg Arg Asp Asn Leu His Ser
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly His Thr Ser Leu Lys Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Ser Gly His Leu Ser Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Asp Asn Leu Ala Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Asn Val Ser Arg Pro Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ser Gly His Leu Ser Arg
1               5

<210> SEQ ID NO 13
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 13

Arg Trp Gln Tyr Leu Pro Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Arg Ser Ala Leu Ala Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Arg Ser Asn Leu Thr Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ser Gly Asn Leu Ala Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Thr Cys Cys Leu Ala His
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ser Asp Asp Leu Thr Arg
1               5
```

```
<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ala Ala Thr Leu Ser Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ser Asp His Leu Ser Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Arg Ser Asp Leu Ser Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Arg Ser His Leu Ala Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Ser Gly Asp Leu Thr Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Gln Ser Gly Asn Leu His Val
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ser Gly His Leu Ala Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Arg Tyr Asp Leu Met Thr
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ser Asp Ser Leu Leu Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Arg Glu Tyr Arg Gly Lys
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Ser Ser His Leu Thr Arg
1               5

<210> SEQ ID NO 30
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 30

Gln Ser Ser Asp Leu Thr Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Leu Asp Ile Leu Gln Gln
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ser Asp Asn Leu Ser Thr
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Asn Ser Tyr Leu Pro Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Arg Ser Asn Leu Ser Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Arg Gln Asp Leu Lys Arg
1               5
```

```
<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Asn Ser Asn Arg Ile Asn
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ser Ser Asp Leu Ser Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Lys Trp Asn Leu Arg Ala
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Lys Gly Thr Leu Gly Glu
1               5

<210> SEQ ID NO 40
<211> LENGTH: 28
<212> TYPE: DNA
<213> ORGANISM: Unknown
<220> FEATURE:
<223> OTHER INFORMATION: Description of Unknown:
      CISH target site sequence

<400> SEQUENCE: 40
ggaaggcccc agcaggcaag ggctgcat                                          28

<210> SEQ ID NO 41
<211> LENGTH: 28
<212> TYPE: DNA
<213> ORGANISM: Unknown
<220> FEATURE:
<223> OTHER INFORMATION: Description of Unknown:
      CISH target site sequence

<400> SEQUENCE: 41
```

-continued gaggaggtgg cagagggtac cccagccc                                28

<210> SEQ ID NO 42
<211> LENGTH: 28
<212> TYPE: DNA
<213> ORGANISM: Unknown
<220> FEATURE:
<223> OTHER INFORMATION: Description of Unknown:
      CISH target site sequence

<400> SEQUENCE: 42
ccagcaaagg acgaggtcta gaaggcag                                28

<210> SEQ ID NO 43
<211> LENGTH: 28
<212> TYPE: DNA
<213> ORGANISM: Unknown
<220> FEATURE:
<223> OTHER INFORMATION: Description of Unknown:
      CISH target site sequence

<400> SEQUENCE: 43
gtggagcgga ctgggcagcg gcccctgt                                28

<210> SEQ ID NO 44
<211> LENGTH: 28
<212> TYPE: DNA
<213> ORGANISM: Unknown
<220> FEATURE:
<223> OTHER INFORMATION: Description of Unknown:
      CISH target site sequence

<400> SEQUENCE: 44
gatgcgtggc ctggacaagc agttggag                                28

<210> SEQ ID NO 45
<211> LENGTH: 28
<212> TYPE: DNA
<213> ORGANISM: Unknown
<220> FEATURE:
<223> OTHER INFORMATION: Description of Unknown:
      CISH target site sequence

<400> SEQUENCE: 45
gagtccagac ggaagctgga gtcggcat                                28

<210> SEQ ID NO 46
<211> LENGTH: 28
<212> TYPE: DNA
<213> ORGANISM: Unknown
<220> FEATURE:
<223> OTHER INFORMATION: Description of Unknown:
      CISH target site sequence

<400> SEQUENCE: 46
atagtgctgc acaaggctga ccacatcc                                28

<210> SEQ ID NO 47
<211> LENGTH: 28
<212> TYPE: DNA
<213> ORGANISM: Unknown
<220> FEATURE:
<223> OTHER INFORMATION: Description of Unknown:
      CISH target site sequence

<400> SEQUENCE: 47

```
ccggaaaggc caggatgcgt ggcctgga                                       28
```

<210> SEQ ID NO 48
<211> LENGTH: 1100
<212> TYPE: DNA
<213> ORGANISM: Unknown
<220> FEATURE:
<223> OTHER INFORMATION: Description of Unknown:
      CISH sequence

<400> SEQUENCE: 48

```
atgggtcctc cactcactgc tcatccactg ccttctagac ctcgtccttt gctggctgtg    60
gagcggactg ggcagcggcc cctgtgggcc ccgtccctgg aactgcccaa gccagtcatg   120
cagcccttgc ctgctggggc cttcctcgag gaggtggcag agggtacccc agcccagaca   180
gagagtgagc caaaggtgct ggacccagag gaggatctgc tgtgcatagc caagaccttc   240
tcctaccttc gggaatctgg tgagtctgag gggggaggca ggccttttcc tgagtagtct   300
ggtgggagaa gcttagttct gcctttgagt ctgatttggg aggcatagcc cggcccagga   360
gagtctgatg ggagaggcac agccctctct agggaagcgt gaagctggag gcactgcctt   420
gacttgcact ggattggtta ccccagctaa tttccactat gtcccttggc ccctctgca    480
cttgcctagg ctggtattgg ggttccatta cggccagcga ggcccgacaa cacctgcaga   540
agatgccaga aggcacgttc ttagtacgtg acagcacgca ccccagctac ctgttcacgc   600
tgtcagtgaa aaccactcgt ggccccacca atgtacgcat tgagtatgcc gactccagct   660
tccgtctgga ctccaactgc ttgtccaggc acgcatcct ggcctttccg gatgtggtca    720
gccttgtgca gcactatgtg gcctcctgca ctgctgatac ccgaagcgac agccccgatc   780
ctgctcccac cccggccctg cctatgccta aggaggatgc gcctagtgac ccagcactgc   840
ctgctcctcc accagccact gctgtacacc taaaactggt gcagcccttt gtacgcagaa   900
gcagtgcccg cagcctgcaa cacctgtgcc gccttgtcat caaccgtctg gtggccgacg   960
tggactgcct gccactgccc cggcgcatgg ccgactacct ccgacagtac cccttccagc  1020
tctgactgta cggggcaatc tgcccaccct cacccagtcg caccctggag gggacatcag  1080
ccccagctgg acttgggccc                                             1100
```

<210> SEQ ID NO 49
<211> LENGTH: 9
<212> TYPE: PRT
<213> ORGANISM: Unknown
<220> FEATURE:
<223> OTHER INFORMATION: Description of Unknown:
      'LAGLIDADG' family peptide motif sequence

<400> SEQUENCE: 49

Leu Ala Gly Leu Ile Asp Ala Asp Gly
1               5

<210> SEQ ID NO 50
<211> LENGTH: 32
<212> TYPE: DNA
<213> ORGANISM: Unknown
<220> FEATURE:
<223> OTHER INFORMATION: Description of Unknown:
      CISH sequence

<400> SEQUENCE: 50

```
ggaaaggcca ggatgcgtgg cctggacaag ca                                  32
```